US010834949B2

(12) United States Patent
Benmoussa

(10) Patent No.: US 10,834,949 B2
(45) Date of Patent: Nov. 17, 2020

(54) METHOD OF MICROALGAL BIOMASS PROCESSING FOR HIGH-VALUE CHEMICALS PRODUCTION, THE RESULTING COMPOSITION OF BUTYROGENIC ALGAL SLOWLY FERMENTING DIETARY FIBER, AND A WAY TO IMPROVE COLON HEALTH USING A SLOWLY FERMENTING BUTYROGENIC ALGAL DIETARY FIBER

(71) Applicant: Mustapha Benmoussa, Albany, NY (US)

(72) Inventor: Mustapha Benmoussa, Albany, NY (US)

( * ) Notice: Subject to any disclaimer, the term of this patent is extended or adjusted under 35 U.S.C. 154(b) by 0 days.

(21) Appl. No.: 16/600,559

(22) Filed: Oct. 13, 2019

(65) Prior Publication Data

US 2020/0046003 A1 Feb. 13, 2020

Related U.S. Application Data

(62) Division of application No. 15/936,357, filed on Mar. 26, 2018, now Pat. No. 10,485,253.

(60) Provisional application No. 62/547,967, filed on Aug. 21, 2017, provisional application No. 62/549,469, filed on Aug. 24, 2017.

(51) Int. Cl.
| | |
|---|---|
| *A23L 17/60* | (2016.01) |
| *A23L 33/21* | (2016.01) |
| *A23L 5/30* | (2016.01) |
| *A61K 31/715* | (2006.01) |
| *A61K 36/05* | (2006.01) |
| *B01D 11/02* | (2006.01) |
| *B01D 21/26* | (2006.01) |
| *C11B 1/04* | (2006.01) |
| *C11B 1/10* | (2006.01) |
| *C11B 3/00* | (2006.01) |
| *C12N 1/12* | (2006.01) |

(52) U.S. Cl.
CPC ............... *A23L 17/60* (2016.08); *A23L 5/32* (2016.08); *A23L 33/21* (2016.08); *A61K 31/715* (2013.01); *A61K 36/05* (2013.01); *B01D 11/0265* (2013.01); *B01D 11/0288* (2013.01); *B01D 21/26* (2013.01); *C11B 1/04* (2013.01); *C11B 1/10* (2013.01); *C11B 3/001* (2013.01); *C12N 1/12* (2013.01); *A23V 2002/00* (2013.01); *A61K 2236/11* (2013.01); *A61K 2236/15* (2013.01); *A61K 2236/50* (2013.01)

(58) Field of Classification Search
CPC . A23L 17/60; A23L 33/21; A23L 5/32; B01D 21/26; B01D 11/0265; B01D 11/0288; A61K 36/05; A61K 31/715; A61K 2236/50; A61K 2236/15; A61K 2236/11; C11B 3/001; C11B 1/10; C11B 1/04; C12N 1/12; A23V 2002/00
USPC ........................................................... 514/54
See application file for complete search history.

(56) References Cited

U.S. PATENT DOCUMENTS

| | | | |
|---|---|---|---|
| 7,700,139 B2 | 4/2010 | Bird et al. | |
| 8,066,793 B2 | 11/2011 | Sinclair | |
| 8,497,229 B2 | 7/2013 | van Boxtel-Verhoeven | |
| 8,506,671 B2 | 8/2013 | Schaafsma | |
| 8,877,472 B2 | 11/2014 | Medoff | |
| 9,012,363 B2 | 4/2015 | van Boxtel-Verhoeven | |
| 9,192,573 B2 | 11/2015 | Inoue et al. | |
| 9,375,703 B2 | 6/2016 | Harlin | |
| 9,517,444 B2 | 12/2016 | Medoff | |
| 9,668,991 B1 | 6/2017 | Cahan | |
| 9,718,738 B2 | 8/2017 | Iwig | |
| 9,758,757 B2 | 9/2017 | Harlin | |
| 9,854,810 B2 | 1/2018 | Meeder | |
| 9,856,178 B2 | 1/2018 | Burnham | |
| 9,988,318 B2 | 6/2018 | Schrader | |
| 10,000,402 B2 | 6/2018 | Ju | |
| 10,023,825 B2 | 7/2018 | Arhancet | |
| 10,163,535 B2 | 12/2018 | Medoff | |

(Continued)

FOREIGN PATENT DOCUMENTS

| | | |
|---|---|---|
| AU | 2017200343 B2 | 2/2017 |
| WO | 2011109900 A1 | 9/2011 |

(Continued)

OTHER PUBLICATIONS

Chen, Paul, et al. "Review of biological and engineering aspects of algae to fuels approach" International Journal of Agricultural and Biological Engineering 2.4 (2010): 1-30.

(Continued)

*Primary Examiner* — Yih-Horng Shiao
(74) *Attorney, Agent, or Firm* — D'Hue Law LLC; Cedric A. D'Hue

(57) ABSTRACT

A method to process microalgae biomass and produce high-value chemicals from microalgae biomass is disclosed. The method uses the same biomass cells to extract more than one component such as lipids, water-soluble chemicals, carotenoids, polysaccharides and algae meal. The method is a sequence of physical and chemical treatments. Water soluble polysaccharides produced by the method exhibit properties of low viscosity at low shear thinning. A method for extracting dietary fiber from microalgal biomass is disclosed. Compositions of water-soluble polysaccharides that are fermented slowly by colon microbiota with less gas production than commercial dietary fiber FOS are disclosed. The present inventions described herein provide a method of improving colon health by increasing butyrate during a microalgal dietary fiber fermenting process by colonic microbiota.

24 Claims, 11 Drawing Sheets

(56) References Cited

U.S. PATENT DOCUMENTS

| | | |
|---|---|---|
| 10,173,936 B2 | 1/2019 | Fiato |
| 10,286,026 B2 | 5/2019 | Israelsen |
| 10,322,395 B2 | 6/2019 | Kumar |
| 10,485,253 B2 | 11/2019 | Benmoussa |
| 10,533,154 B2 | 1/2020 | Rong |
| 10,611,854 B2 | 4/2020 | Pruvost et al. |
| 2010/0050502 A1 | 3/2010 | Wu et al. |
| 2013/0122180 A1 | 5/2013 | Brooks et al. |
| 2015/0368684 A1 | 12/2015 | Medoff |
| 2017/0233499 A1 | 8/2017 | Pruvost et al. |
| 2018/0044664 A1 | 2/2018 | Wigley |
| 2018/0258005 A1 | 9/2018 | Benmoussa |
| 2018/0258231 A1 | 9/2018 | Lavoisier |
| 2018/0282826 A1 | 10/2018 | Mirsiaghi |
| 2018/0326073 A1 | 11/2018 | Mooney |
| 2019/0008157 A1 | 1/2019 | Shinde |
| 2019/0053523 A1 | 2/2019 | Benmoussa |
| 2019/0335761 A1 | 11/2019 | Faugeron-Girard |
| 2020/0008379 A1 | 1/2020 | Ayers |
| 2020/0060283 A1 | 2/2020 | Shinde |
| 2020/0060288 A1 | 2/2020 | Shinde |
| 2020/0079701 A1 | 3/2020 | Blotsky et al. |
| 2020/0102457 A1 | 4/2020 | Goldstein et al. |

FOREIGN PATENT DOCUMENTS

| | | |
|---|---|---|
| WO | 2014144588 A1 | 9/2014 |
| WO | 2015150645 A1 | 10/2015 |
| WO | 2016029113 A1 | 2/2016 |
| WO | 2016059058 A1 | 4/2016 |
| WO | 2017117297 A1 | 7/2017 |

OTHER PUBLICATIONS

Park, Ji-Yeon, et al. "Advances in direct transesterification of algal oils from wet biomass." Bioresource technology 184 (2015): 267-275.

USPTO, Notice of Restriction and Election of Species Requirement for U.S. Appl. No. 15/936,357, dated May 2, 2019.

Mustapha Benmoussa, Response to Restriction and Election of Species Requirement for U.S. Appl. No. 15/936,357, dated May 2, 2019, 6 pages.

USPTO, Notice of References Cited, including IDS, for U.S. Appl. No. 15/936,357, dated Jul. 9, 2019, 19 pages.

USPTO, Non-Final Office Action for U.S. Appl. No. 15/936,357, dated Jul. 10, 2019, 73 pages.

USPTO, Applicant Initiated Examiners Interview Summary, including Applicants Proposed Amendment, for U.S. Appl. No. 15/936,357, dated Aug. 13, 2019, 17 pages.

Mustapha Benmoussa, Response to Office Action dated Jul. 10, 2019 for U.S. Appl. No. 15/936,357, dated Oct. 1, 2019, 3 pages.

USPTO, Notice of Allowance for U.S. Appl. No. 15/936,357, dated Oct. 9, 2019, 23 pages.

USPTO, Restriction for U.S. Appl. No. 15/844,481, dated Apr. 1, 2020, 6 pages.

Applicant, Response to Restriction for U.S. Appl. No. 15/844,481, dated Apr. 17, 2020, 7 pages.

USPTO, Non-Final Office Action, List of References Cited for U.S. Appl. No. 15/844,481, dated Jun. 26, 2020, 23 pages.

|       | 0h | 6h   | 12h  | 24h  |
|-------|----|------|------|------|
| Blank | 0  | 0    | 0    | 0    |
| FOS   | 0  | -0.5 | -0.6 | -0.6 |
| MWSF  | 0  | -0.3 | -0.4 | -0.4 |

FIG. 11

METHOD OF MICROALGAL BIOMASS PROCESSING FOR HIGH-VALUE CHEMICALS PRODUCTION, THE RESULTING COMPOSITION OF BUTYROGENIC ALGAL SLOWLY FERMENTING DIETARY FIBER, AND A WAY TO IMPROVE COLON HEALTH USING A SLOWLY FERMENTING BUTYROGENIC ALGAL DIETARY FIBER

CROSS REFERENCE

This application is a divisional of U.S. Non-Provisional application Ser. No. 15/936,357, filed Mar. 26, 2018, which claims the benefit of U.S. Provisional Application No. 62/547,967, filed Aug. 21, 2017, and U.S. Provisional Application No. 62/549,469, filed Aug. 24, 2017. This application expressly incorporates by reference each of these patent applications.

FIELD

In one aspect, the present invention is related to a method of extracting chemicals from microalgal biomass such as *Botryococcus braunii*. In another aspect, the present invention is related to the use of a water-soluble polysaccharide, extracted from microalgal biomass such as *Botryococcus braunii*, to improve and maintain colon health.

BACKGROUND

Food security and energy for transportation are global concerns due to increased population and decreased fossil fuel resources. Countries that produce and export oil are not even safe from the depletion of oil and the socioeconomic consequences. Land crops are an alternative to fossil fuels and are a source of oil for biofuels like bioethanol, biodiesel and jet fuels. However, many other market segments, such as human and animal nutrition, also use land crops as a source of raw materials. Unfortunately, land surface for agriculture is diminishing, while global population is growing. Global population is estimated to be around 9.3 billion in 2025. Growing worldwide populations are expected to increase food and energy demand (Wheeler and von Braun, 2013). But land crops cannot respond to both increased energy and food demand in the future. Lobell et al. (2008) reported that south Asia and southern Africa are two regions that will be negatively impacted by climate change and will likely suffer from decreased production before crops can adapt. Moreover, the demand for biodiesel results in an increase of land crops for energy production (Panichelli et al., 2015). A major challenge to global food and energy security is global population growth and the use of land crops for renewable energy (Lele et al., 2013). A source of energy that is non-competitive with food is feasible and more sustainable, both are necessary for worldwide acceptance.

Microalgae is a non-competitive alternative that will complement land crops and has the potential to alleviate concerns about energy and food security. Microalgae can play a significant role in climate change mitigation without any potential conflicts with food security. Microalgae is a source of food and renewable energy. Microalgae biomass can be produced in any country that has fresh or salt water. Land which is not suitable for agriculture can produce microalgae biomass, it is the only crop producible using salt, brackish wastewater and non-arable land. Microalgae is a micro-crop, it grows fast and yields 50 times more biomass than any other land crop. Microalgae cells use sun light to convert $CO_2$ into chemical energy. It has the potential to accumulate over 50% (DW) of oil. Microalgae biorefineries will significantly impact socioeconomic development and simultaneously solve problems in both bioenergy and food security. Thus, microalgae is a sustainable means to overcome global food, energy, environment and socioeconomic concerns.

Microalgae biomass is a potential feedstock for production of sustainable biofuels and nutraceuticals. Microalgae biorefineries produce biochemicals with health benefits. Many chemicals can be extracted from microalgae biomass including oil for biofuels, omega-3/6/9 oil, water-soluble chemicals, carotenoids, proteins, and polysaccharides. Animal feed is also produced from the microalgae biomass. Production of biofuels is a national interest due to food and energy concerns. The microalgae industry will benefit society and the economy by solving problems in food and energy.

However, it has been reported that it is not yet commercially feasible to produce biofuels via microalgae as feedstock (Demirbas, 2011; Rawat et al., 2013; Stephens et al., 2010). The design of the microalgae biorefinery should involve high-value chemicals production and reduce capital investment and operating expenses.

The Microalgal Biorefinery

The microalgae biorefinery utilizes a multistep process including biomass production, harvesting, drying, oil extraction, and further processing of residual biomass. Many biomass production technologies have been reported (Elser et al. 2017). There are open and closed systems, mainly including open pond (Chisti, 2010), photobioreactor, and fermenter (Oncel and Kose, 2014) respectively. Recently, combinations of two production systems have been reported, such as a photobioreactor-open pond, fermenter-photobioreactor, or fermenter-open pond (Moody et al., 2014; Rawat et al., 2013). Generally, the open pond method utilizes a raceway pond in a closed-up channel with an oval shape, open to the air. The pond is mixed with a paddle and the water is 0.20 to 0.4 m deep. Photobioreactor (PBR) and fermenter are tools to produce biomass under controlled conditions. PBR uses sunlight alone or both sunlight and organic carbon, whereas the fermenter only uses organic carbon as the source of energy.

Biomass harvesting is the second step in the microalgae biorefinery process. After a period of microalgae growth, the biomass concentration is high enough to create a shading effect, which can impact light efficiency and biomass yield. The biomass is harvested using physical or chemical tools. The physical harvesting involves centrifugation, sedimentation, filtration, chemical flocculation, or bio-flocculation (Brennan et al., 2010; Bilad et al., 2012). Chemical flocculation is performed using pH adjustment and metal ions such as $Fe^{3+}$ or $Mg^{2+}$ (Brennan et al., 2010; Yang et al., 2011; Sharma et al., 2013). Some processing technology requirements require drying the biomass before extraction. Pretreatment of harvested biomass is an extra step which can increase product content and improve processing yield.

The extraction of end products is the last step in the biorefinery process. This process can be performed using wet or dried biomass. Biomass processing involves destructive and non-destructive techniques. A milking process is the extraction of oil by non-destructive techniques, it allows for continuous biomass growth and in some cases continuous milking (Ramachandra et al., 2009). Destructive oil extraction is the most used in the laboratory, pilot and commercial scale (Wang and Yuan, 2014, Ranjith et al. 2015). Destructive extraction of oil and other compounds uses both wet and dried biomass (Lee et al., 2009, Rodolfi et al., 2009). It involves a disruption of the cell wall and the membrane by solvent and/or physical means (Halim et al., 2012; Bligh & Dryer 1959; Patil et al., 2011). Commercial processors most often use hexane as the solvent and recycle it by distillation. Extracted oils are used as a commodity or converted to biofuel. Transesterification of the extracted oils produces biodiesel. Catalytic cracking of the extracted oils produces aircrafts fuel. By-products can also be extracted with further processing. Moreover, residual microalgae biomass after oil extraction can be used as animal and fish feed, which makes algae a valuable input for livestock and aquaculture industry.

Capital investment and operation expenses are the main constraints when starting a biorefinery. Fiscally breaking even is the first critical step in the economics of the biorefinery, the second step is generating positive cash flow. Biomass production and processing are cost-challenging steps in the initial expenditure phase. Chisti (2010) reported that sustainable microalgae biofuel production depends on cutting the actual cost by 10 times. Commercial biorefineries need to minimize capital and operation costs and maximize the yield of by-products. In order for the microalgae industry to be commercially feasible, it is necessary to reduce the expenditure in biomass production and its processing and increase sales of high value by-products also called high-value chemicals. By-products mainly include proteins, polysaccharides, omega-3, carotenoids compounds and biofuels. It is well known that these natural products provide high nutritive values with health care benefits. Thus, they have wide support from the academic community, nutritionists and consumers (Privadarshani et al., 2012; Ali & Saleh, 2012). High-value by-products are the main source of cash flow. They can be an exit strategy toward a feasible commercial biorefinery.

High-Value Chemicals

Microalgae is a sustainable natural feedstock. Microalgae is a source of bioactive compounds such as fatty acids, proteins, polyphenols, carotenoids, vitamins, and polysaccharides. These compounds have potential applications in pharmaceutical, nutraceutical, food, drinks, animal feed, bioenergy and cosmetic fields.

Proteins and Fatty Acids

Many studies have shown that microalgae strains are rich in polyunsaturated fatty acids (PUFAs), polyphenol, and carotenoids (Herrero et al, 2013, Eom & Kim 2012). *Spirulina* is a model of the commercial application to the algae biomass industry. *Spirulina platensis* is generally served as a supplement for its protein content and other bioactive components. *Spirulina* is rich in proteins (55% to 70%) (Ouhtit et al., 2014, Ali & Saleh, 2012). Food supplements can utilize protein directly from whole algae cells or after extraction. Microalgae meal is easy to dry after oil extraction, it can be stored at room temperature, and it is rich in proteins and other beneficial health components.

Essential fatty acids are not synthesized by the human body and must be provided in the diet. These fatty acids include alpha-linolenic acid (ALA), linoleic acid (LA), eicosapentaenoic acid (EPA) and docosahexaenoic acid (DHA). The Mediterranean diet is rich in ALA, and populations who are using the Mediterranean diet are more resistant to cardiovascular disease (Simopoulos, 2008). Rabinovitz et al. showed the importance of LA/ALA ratio in the diet (Rabinovitz et al., 2004). Djoussé et al. (2003) reported an association between ALA consumption and a lower risk of carotid atherosclerosis.

Polysaccharides

There are water-soluble and insoluble polysaccharides groups. Generally, soluble polysaccharides include hemicellulose, pectin, gum, β-glucan and novel fibers. Insoluble fibers include cellulose, lignin, chitin, chitosan and some hemicellulose. Insoluble fibers are known by the decrease of the transit time through the gastrointestinal system, the increase of the fecal bulk, and it is associated with increased secretion of bile acids (Brouns et al., 2002). Water-soluble fibers are known by an increase of the transit time and a delay in gastric emptying.

Macroalgal polysaccharides include agar, carrageenan, and alginate. They are easily isolated from macroalgae because of their ability to bind water, form a gel, and to form and stabilize emulsions. The development of viscous gels depends on the concentration of soluble fibers, and their structure and viscosity properties. Macroalgal polysaccharides are used as stabilizers, water-thickeners, emulsifiers, and gelling agents in food, beverages, pharmaceutical, cosmetics, paper, and textiles industries (Milani et al., 2012; de Jesus Raposo et al., 2015).

Seaweed (aka macroalgae) has shown that it is a sustainable source of polysaccharides, and the global market is well developed with many commercial applications. The macroalgal polysaccharide market is a $1 billion USD industry including alginate, agar, and carrageenan (Burtin 2003). The whole macroalgal industry offers a variety of products with a total annual production value of about $6 billion USD, including $5 billion as products for human consumption. For example, the price of pharmaceutical grade alginate is $13.00 to $15.50 per kg and food grade is $6.50 to $11.00 per kg. Unfortunately, the microalgae polysaccharide industry is not as developed. The main key factor in future developments in the commercial microalgal polysaccharide industry is the feasibility of biomass production and the polysaccharide extraction process.

It has been reported that total polysaccharides content of seaweeds can reach 75% of the dry weight, which is higher than the fiber content of most fruits and vegetables (Jimenez-Escrig and Sanchez-Muniz, 2000). The cell wall is built mainly with cellulose, hemicellulose and neutral polysaccharides in order to support the tall structure in water (Gómez-Ordóñez et al., 2010). The structure of the cell wall in seaweed is less rigid than in the land crops and microalgae, which make the polysaccharides easier to extract. Seaweed polysaccharides are generally involved in food, beverages, pharmaceutical and nutraceutical industry. Macroalgae polysaccharides are species specific. Green algae contain starch, xylan, mannan, ionic polysaccharides, sulphuric acid polysaccharides, and sulphated galactans (Zaporozhets et al., 2014). Red algae contain agar, carrageenan, xylan, floridean starch, water-soluble sulphated galactan, and porphyran as mucopolysaccharides (Kraan, 2012). Brown algae are known for their content in alginates, fucan, laminaran, and sargassan (Bocanegra et al., 2009).

Macroalgae biomass and products have been used for many centuries as food and in traditional medicine. Many studies report the association between consuming macroalgae products, and a health benefit (Lovegrove et al., 2017; Hamed et al., 2015; Costa et al., 2010). Macroalgae fibers are anionic polysaccharides; some are only a little fermented and others are not fermented by human gut microbiota (Fåk et al., 2015). One study showed that fibers from macroalgae are less fermented and produce less short chain fatty acids (SCFA) than those from plants (Murata & Nakazoe, 2001).

Algal polysaccharides are known by their broad bioactive properties. Many viscous-soluble polysaccharides have been correlated with hypocholesterolemic and hypoglycemic effects. While water-insoluble polysaccharides, mainly cellulose, have been reported to be associated with a decrease of the digestive tract transit time (Holdt & Kraan 2011). Fucoidans, aka sulfated polysaccharides, are involved extensively in the cell walls of brown macroalgae. In addition to the impact on the inflammatory and immune systems, fucoidans demonstrated many physiological and biological features, such as antitumor, anticoagulant, antioxidant, antiviral, and antithrombotic activities (Wijesekara et al., 2011). Fucoidan has gelling properties, and it has been used as a dietary complement as well as an antioxidant (Heim et al., 2014). Porphyran, another sulfated polysaccharide, is the major component of the red macroalgae *Porphyra*. As a second main source of glucan in brown algae, laminarin plays a regulator role of the intestinal metabolism through its impacts on mucus structure, intestinal pH, and SCFA formation (Smith et al., 2011; Holdt & Kraan 2011). Polysaccharides show anti-herpetic bioactivity; they are potent as an anticoagulant and decrease low-density lipid (LDL)-cholesterols in rats (hypercholesterolemia); they prevent obesity, large intestine cancer and diabetes; and they have antiviral activities (Mišurcová et al., 2012, Matloub et al., 2015, Brown et al., 2012, Karmakar et al., 2010; Vera et al., 2011).

Microalgae cell wall structure is built to protect the cell components and hold its structure and morphology. The cell wall is hard to disrupt and needs aggressive treatment. The structure of the cell wall is a determinant factor in polysaccharide extraction cost. Many techniques have been used to extract polysaccharides from macroalgae. Generally, the sulfated polysaccharides extraction procedure involves a preliminary treatment with a solvent to remove lipids and pigments, followed by proteolysis under acid or alkaline conditions (Fidelis et al., 2014). Recently, physical pre-treatments such as ultrasound sonication and assisted microwave techniques were used instead of chemical pre-treatment to improve polysaccharides yield (Rodriguez-Jasso et al., 2011). Laminarian extraction involve treatments such as grinding and ultrasound assisted extraction (Kadam et al., 2015).

Alginates are extracted from brown macroalgae and can be in the acid or salt form. The acid form is called alginic acid, which is linear polyuronic acid units, and the salt form is a cell wall component constituting 40 to 47% of the dry weight biomass (Draaisma et al., 2013). They are many research report and patents on alginates extraction process from brown macroalgae. However, further detail of any successful commercial extraction process was not reported before (Bothara et al., 2012). Most commercial extractions involve preliminary treatment, grinding, alkaline extraction, calcium or acid precipitation, followed by bleaching and washing steps, and then drying at 42° C. To make the extraction process commercially feasible, they use sodium bicarbonate at pH 10 with grinding and a screen to separate soluble sodium alginate followed by addition of calcium chloride to precipitate sodium alginate in the fibrous form of calcium alginate. Recently, a pilot plant scale extraction was described from the preliminary treatment to the end-product (Hernández-Carmona et al., 1999; McHugh et al., 2001). The authors used 0.1% formalin solution as overnight preliminary treatment with the ratio of biomass to the solution at 1:9, and then drained and washed with hydrochloridric solution at pH 4 for 15 min. The biomass is heated at 80° C. for 2 hours with constant stirring in a sodium carbonate solution at pH 10 and a ratio of 1:16.6 biomass to the solution, and then it is filtrated. Sodium alginate in suspension is precipitated in 10% calcium chloride. The quantity of required calcium chloride is estimated to 2 parts per 1 part alginate. The precipitate was filtrated using a metal screen (18 mesh). The residual calcium chloride is measured by complexometric titration (Yappert and DuPre, 1997) to optimize the ratio calcium to alginate. Calcium alginate is bleached in sodium hypochlorite solution (5%) and converted to alginic acid with three times washings at pH 1.8 for 15 min each, then the pH is adjusted to 7 using sodium carbonate, and dried at 50° C.

Pigments

The color appearance of algae depends on the type of pigmentation. The primary role of pigments in the photosynthesis process is to absorb visible light and to initiate reactions. Chlorophylls, carotenoids, and phycobilins are the three major groups of pigments. The color changes during the life cycle of crops depending on the content of these pigments. The green color is influenced by the high content of chlorophylls. Yellow and orange color is depending on the content of carotenoids, which are high in microalgae and macroalgae. Phycobilins are dominant in cyanobacteria.

Chlorophylls are known by their greenish color. Chlorophyll a is the primary pigment in the photosynthesis chain and serves as a first electron donor. Chlorophylls b, c, and d are considered accessory pigments. Carotenoids are known for their health benefits, Lutein and zeaxanthin have been reported to reduce the incidence of the age-related macular degeneration (Schalch et al., 2007).

Carotenoids are localized in or attached to the chloroplast membrane. Their main role is to protect the chloroplast membrane components against photo-oxidative damage when there is an excess of solar energy. The antioxidant properties of carotenoids distinguish them from other pigments. Generally, carotenoids are water-insoluble molecules attached to the membrane. Thus their extraction is performed by solvents. The carotenoids are divided based on structure into two classes: carotenes and xanthophylls. Carotenes are hydrocarbons, and xanthophylls are known by their oxygenated functional groups. Since they are hydrocarbons, and therefore contain no oxygen, carotenes are fat-soluble and insoluble in water. In contrast with other carotenoids, xanthophylls contain oxygen and thus are less chemically hydrophobic. Xanthophyll molecules are more polar than carotenes. The major types of carotenoids classes are lutein, β-carotene, canthaxanthin, zeaxanthin, lycopene, and astaxanthin. Astaxanthin antioxidant activity is 10 times higher than β-carotene (Naguib, 2000).

Carotenoids have been used in food, beverages, cosmetics, coloring, and supplements industries. Carotenoids global market is estimated to reach $1.53 Billion by 2021 (Persistence Market Research 2017). Carotenoids have been found in many organisms. Microalgae show a high content of carotenoids and have created a wide interest. *Dunaliella salina* accumulates β-carotene up to 14% dry weight (DW), and *Haematococcus pluialis* is rich in astaxanthins (2-3% DW) (Ibañez et al., 2011). The high content of lutein in *Chlorella vulgaris* had been reported by Lordan and Stanton (2011).

***Dietary Fiber Health Benefits

Epidemiological and clinical studies demonstrate that diets rich in dietary fiber reduce chronic disease risks and improve individual well-being (Anderson et al., 2009; Bindels et al., 2015; Jiménez-Escrig, et al., 2000). They reported numerous health benefits gains after consuming a diet rich in dietary fibers. Dietary fibers have also been linked with beneficial health effects in gastrointestinal inflammatory disorders and colon cancer prevention (West et al., 2015). A daily intake of the recommended dose of dietary fiber, for example over 20 g/d, can inverse adverse health effects. Other health benefits have also been identified, such as reducing risks of cardiovascular disease, immune system and type 2 diabetes (Stephen et al., 2017). High dietary fiber intake is associated with improvement of glycemic response and insulin sensitivity, and contributes to the overall energy intake management (Nicolucci et al., 2015). Unfortunately, many adverse effects were also reported in individuals who are consuming a diet poor in dietary fiber or taking an inadequate dose of dietary fiber. Adverse effects include high risk of obesity (Tweney et al., 2017), type 2 diabetes (Gulati and Misra, 2017), inflammatory bowel disease (Sheehan et al., 2015), colon cancer (Mehta et al., 2017; Navarro et al., 2016) and cardiovascular disease (Lu et al., 2017).

Dietary guidelines for fiber intake vary and depend on different parameters, including age. Generally, the recommended daily intake range is between 25 g/d and 38 g/d (Stephen et al., 2017). The average daily intake of dietary fibers among the U.S. population ranges between 14.1 g/d and 17.8 g/d, well below the recommended daily intake range (Zhang et al., 2015). The low daily intake of dietary fiber may be associated with many adverse health issues and chronic disease risk factors (Zhang et al., 2015). Survey data show high rates of people in the U.S. population are expected to exhibit symptoms of chronic disease (Dai et al., 2017). Chronic diseases are the leading cause of death in the United States (Seigel et al., 2016).

Dietary fibers are carbohydrate polymers. Their hydrolysis generates free carbohydrate units that are metabolized by cells, such as colonic bacteria. A major component of plant cell walls is carbohydrate polymers including cellulose, hemicellulose, and pectin. Carbohydrate polymers are also extracted from seaweed. Cellulose is the most abundant carbohydrate polymer in land crops and consists of glucose monomer. Cellulose is a water-insoluble polymer; it improves fecal volume and colonic movement where it is partially fermented by gut microbiota (Bishehsari et al., 2018). Hemicellulose polymer consists of pentose and hexose monomers. Pentose includes xylose and arabinose. Hexose includes galactose, glucose, manose, rhamnose, glucuronic and galacturonic acids. Pectin polymer is also formed by pentose and hexose units and known for their health benefits (Kay, 1982). The degree of polymerization of oligosaccharides is between 3 to 10 units. Oligosaccharides are mainly found in fruits and seeds. The most popular oligosaccharides are fructooligosaccharides (FOS), galactooligosaccharides (GOS) and inulin. Their consumption had been reported to be associated with health benefits (Gibson et al., 2017).

Commercial applications and transit time efficiency of dietary fibers are determined by their physical properties. There are two groups of dietary fibers: water-soluble and water-insoluble polysaccharides. Water-insoluble dietary fibers are less fermented or not fermented at all by the colon microbiota. Water-insoluble dietary fibers have a positive role in the digestive system e.g., influencing the food transit time in the small and large intestine and moderating nutrient adsorption. Water-soluble dietary fibers are fermented by the colon microbiota. Water-soluble dietary fibers are often used in the food, beverages, cosmetic, pharmaceutical, and supplement industries. Water-soluble dietary fibers are easy to mix with other ingredients. Water-soluble dietary fibers improve product structure and texture.

The gut (colon) microbiota is an ecosystem of living microorganisms in the human digestive system. The microbiota is a symbiotic interaction between human eukaryotic cells and prokaryotic bacteria in the large intestine. In this symbiotic relationship, the colon is an incubator and fermenter where bacteria find the right temperature and other physical parameters to grow and metabolize non-digested substrates remaining after passing through the small intestine. These non-digested substrates can be carbohydrate, proteins or any other synthesized or biosynthesized chemical component.

Food nutrients which were not digested and absorbed in the small intestine will move to the large intestine (colon) where they will be fermented. Carbohydrate fermentation is a process of converting carbohydrate into end products such as short chain fatty acids (SCFAs), gases, and heat. The major SCFAs are acetic, propionic and butyric acids. Acetate is known by its 2 carbon units, propionates by 3 carbon units, and butyrate by 4 carbon units. Generally, SCFAs are reported to be involved in the gut microbiota energy homeostasis (Rosenbaum et al., 2015). The synthesis of SCFAs is associated with health benefits to the body.

The human colon contains a complex microbiota ecosystem. It was estimated to be $10^4$ bacteria belonging to more than 1000 species (Lozupone et al., 2012). Moreover, the proportion of SCFA content depends on the type of fiber substrate and microbiota (Aguirre et al., 2014). If we want to target specific health benefits or physiological effects, the type of dietary fiber choice is an important parameter. For this purpose, every dietary fiber needs to be characterized and correlated to its impact on colon microbiota composition and metabolism effects. Unfortunately, only a few studies on the effects of each type of dietary fiber have been reported. Yang et al. reported that there is a specific impact for each dietary fiber type on colon microbiota composition and metabolism. Dietary fibers such as pectin, inulin, resistant starch, beta-glucan, arabynoxylan were used in an in vitro study. Fermenting all these dietary fibers is associated with a significant increase of acetate comparatively to propionate and butyrate. Acetate plays a major role in the human body; it serves as a source of energy in peripheral tissues and liver. Moreover, acetate is involved in gluconeogenesis and lipogenesis metabolic pathways as a signaling molecule (Zambell et al., 2003). There is also the differential growth of colonic bacteria. Since most available dietary fibers promote acetate production, there is a need to develop novel dietary fibers that will promote the production of SCFA, especially butyrate. Such dietary fiber will promote and maintain colon microbiota diversity. In this purpose, a microalgal water-soluble dietary fiber is proposed in the present invention.

The study on germ free rate confirmed that SCFAs are essential to colonic cell proliferation and necessary to maintain healthy physiology (Koh et al., 2016, Sakata, 1987). SCFAs are metabolized inside the colon and absorbed and transported in the bloodstream or used by colonic epithelial cells (Macfarlane et al., 2003). Over 95% of SCFAs are absorbed from the colonic lumen (Binder et al., 1989). SCFAs can be considered a significant link between "healthy fiber" and body health benefits (Delcour et al., 2016). SCFAs are preferentially used by colonic mucosa as an energy source. These health benefits of SCFAs are confirmed by many previous reports. Propionate modulates the cholesterol concentration in the blood (Ashraf et al., 2017). Butyrate is a major source of energy in the distal gut for colonocytes and enterocytes (Donohoe et al., 2011), and it protects colonic mucosa and stimulates epithelial cell proliferation (Hamer et al., 2008). These effects improve barrier functions in the distal region of the large intestine (Kelly et al, 2015). It was confirmed that the decrease of bacteria producing butyrate is inversely associated with many colonic diseases including inflammatory bowel disease (Machiels et al., 2013).

An important parameter that can distinguish between dietary fiber groups is the fermenting behavior of dietary fibers. A slowly fermentable dietary fiber is highly desired and is associated with many health benefits. In the gut, a slow fermenting dietary fiber generates less gas than a rapidly fermenting dietary fiber.

Rapidly fermenting dietary fiber is not preferred. The majority, if it is not all, of rapidly fermenting dietary fiber is fermented in the proximal area of the colon. The fermentation rate in the proximal area is enough to generate a high volume of gas, causing bloating and discomfort. The distal region of the colon is almost deprived of dietary fiber. This shortage of carbohydrate in the distal area is generally compensated by proteins. The fermentation of proteins by colon bacteria in the distal area generates toxic metabolites, such as phenols and ammonia.

In contrast, slowly fermented dietary fibers are not totally fermented in the proximal region of the colon. Slowly fermented dietary fibers are fermented along with the colon, creating an environment of detoxification, and producing SCFAs that are adsorbed in both proximal and distal colon regions. Fermentation of slowly fermented dietary fibers throughout the colon can reduce colonic diseases risks and improve colon health.

Most commercially available dietary fibers are rapidly fermenting, such as fructooligosaccharides (FOS). In some cases, the commercially available dietary fibers are poorly fermented such as pectin, and β-glucan. Other dietary fibers are poorly fermenting or non-fermenting such as whole or debris of cell wall, cellulose, etc. The ideal characteristics of dietary fiber are: slowly fermenting, water-soluble, fully metabolized by colon microbiota, and generates bioactive components such as SCFA (especially butyrate).

Cereals, fruits, and vegetables are the main source of dietary fiber in the human diet. There is global population growth and is expected to reach 9.3 billion by 2050. Land crops may not be able to respond to the global food demand in the future. Moreover, dietary fibers from land crops need to be modified to reach the ideal characteristics. There is a need to find or develop other biomass sources for dietary fiber production with these ideal characteristics.

Marine crops may be a sustainable alternative to land crops. Seaweed biomass has already shown the capability to provides polysaccharides (fibers) and other high-value chemicals. Microalgae can be sustainable biomass that is a potential source of dietary fiber and many high-value products. Microalgae are photosynthetic organisms. Microalgae convert carbon dioxide, $CO_2$, into organic molecules using solar energy. Microalgae can grow on any land and use seawater. Microalgae can grow where no other land crop can grow. Microalgae may be a sustainable alternative to classic biomass sources. The daily intake of microalgal dietary fibers may be associated with health benefits that many classic dietary fibers do not provide.

There are previous inventions reporting the role of dietary fiber on the colonic health, especially bowel health and gastrointestinal inflammation. Some of them reported the role of polysaccharides in colonic health. These polysaccharides were extracted from cereals (Hamaker et al. 2014) or on resistant starch (Cummings et al., 1996) and described below.

RELATED PATENTS

The U.S. Published Patent Application No. 2015/0010, 672A1 by Hamaker et al. and published on Sep. 19, 2014, teaches a slowly fermentable soluble dietary fiber. Fermentation of treated bran or hydrolysate product resulted in about 50 percent to about 93 percent by weight arabinoxylans. The bran was selected from the group consisting of corn, wheat, rice, sorghum, and any combination thereof. The study found slow fermentation of dietary fiber is associated with higher level of butyrate production than FOS.

The U.S. Published Patent Application No. 2015/0359, 836A1 by Israelsen and published on Aug. 25, 2015, teaches using both probiotic bacteria and fermented cereal as a treatment for inflammatory bowel diseases, irritable bowel syndrome, and other gastrointestinal disorders. The treatment strategy alleviated the symptoms of inflammatory bowel diseases regardless of a mild, moderate, or severe stage of the disease.

The U.S. Pat. No. 9,579,340A1 by Ritter et al. and issued on Feb. 28, 2017, teaches a prebiotic formulation for treating symptoms associated with lactose intolerance and for overall improvement in gastrointestinal health. The prebiotic is mainly a galactooligosaccharide (GOS).

The U.S. Pat. No. 9,668,992 B1 by Cahan et al., and issued on Jun. 6, 2017, teaches the SCFA composition in the colon. It also teaches composition for treating the colon with a core including at least one SCFA composition or a pharmaceutically acceptable salt or ester thereof.

The U.S. Pat. No. 7,700,139, by Bird et al., issued Apr. 20, 010, teaches a resistant starch that produced a high level of butyrate during fermentation (Bird et al., 2010; U.S. Pat. No. 7,700,139). Unfortunately, the composition does not have the appropriate and necessary physical properties to have many commercial applications in food, beverages, etc.

SUMMARY

The present research project was initiated to develop a commercially viable microalgae biorefinery using a wild *B. braunii* strain. The production of high-value chemicals could be a sustainable alternative in the biorefinery feasibility. The design of a processing line is needed to produce high-value chemicals in a way that will make the microalgae biorefinery a viable industry because current methods for biomass production and oil extraction cost too much to compete with the fossil fuel industry. The major challenge was how to develop a method that allows for selective extraction of each high-value chemical from the same cell at low cost. The project started with the development of microalgae strains with high biomass and oil yield that tolerate environmental changes. In meantime, additional project strategy includes exploring all major cell components that may have some commercial value.

In the biomass production step 100, many techniques were explored including heterotrophic, photoheterotrophic, and phototrophic modes. The goal was to produce biomass with less competition to food. Under the heterotrophic mode, crude glycerol from a biodiesel plant was used as a source of organic carbon. The phototrophic growth mode involves utilizing light energy to convert $CO_2$ into organic molecules. The photoheterotrophic growth mode is a combination of both heterotrophic and phototrophic modes. Biomass is grown 100, and then harvested 101. It is optional to remove water 102 from the harvested biomass. Harvested biomass may be used dry or wet in the slurry 103. In the exemplary embodiment, the use of wet biomass avoided the expense of the biomass drying step and was included in the processing line. Post-harvest treatment 104 was reported to improve oil yield in microalgae. As illustrated in FIG. 1, we utilized a combination of pH 105, osmotic stress 106, and nitrogen starvation, which is pH 9, 50 mM of NaCl and 20 mg/L nitrogen for 3 days.

As illustrated in FIG. 2, the extraction process is a sequence of steps one after another that allow the extraction of the major high-value components from the same cell. The process starts with oil extraction using ultra-sonication 109 of a soft biomass concentrate 103. The oil 112 floating on the top is removed, and the yield was 30% (oil weight/dry biomass). The yield was calculated based on oil weight and dried biomass. Next, the aqueous liquid phase 110 on top of the biomass comprising water-soluble chemicals such as antioxidant and mineral salts was removed. The next step was a hydrothermal treatment 113 of the leftover biomass 111. The hydrothermal treatment 113 is a heating process at 70° C. for 12 hours at high pH using 2M of KOH and 2M of NaOH. The hydrothermal treatment is followed by centrifugation at 2500 rpm for 10 min. The resulting pellet 114 is used for carotenoids extraction and the supernatant 115 for polysaccharides precipitation.

Carotenoids 117 extraction was performed using a solvent such as hexane. The solvent extract was dried and then weighed. The yield was 1.5%. The carotenoids extract 117 color is yellow to orange. As illustrated in FIG. 3, the analysis showed that the carotenoids extract 117 comprises lutein, carotene, and zeaxanthin. After carotenoids extraction, the pH of the biomass in the pellet was adjusted and then processed to be served as animal feed 116 (FIGS. 1 and 2).

Polysaccharides 118 in the supernatant were precipitated in calcium solution (10%) or 70% ethanol solution. Both extraction methods yielded nearly 32% of the biomass. The harvested polysaccharides 118 were washed and pH adjusted to about 7 and then dried for further analysis. As illustrated in FIG. 5, analysis results show that polysaccharides have shear thinning. As illustrated in FIG. 6, low viscosity at low shear stress, and viscosity depend on the temperature during the process.

The extraction process shown above is an environmentally friendly technology that uses almost all the biomass component. The extraction process produces little waste, high-value chemicals, and animal feed. The high-value chemicals include microalgae oil rich in omega-3/6/9, antioxidants, and mineral salt, carotenoids, and water-soluble polysaccharides (FIGS. 1 and 2).

In one embodiment of the invention, the present disclosure teaches an extraction method to isolate all the high-value components of the cell selectively. Another embodiment illustrates a way to extract microalgal water-soluble polysaccharides with relatively, low viscosity at low shear stress.

Shear thinning and viscosity are temperature dependent. The relatively low viscosity at low shear stress properties allows these novel polysaccharides to be easily mixed with other ingredients, pumped, and handled during processing and as an ingredient or end product. Thus in further embodiments, water-soluble polysaccharides with relatively, low viscosity at low shear stress are used as food and beverages ingredients and as supplements with mouthfeel characteristics.

Additional embodiments described herein provide a method for improving colon health by increasing short chain fatty acid concentration such as butyrate in the colon via the use of a slowly fermenting microalgal dietary fiber. The process results in an increase in the SCFAs butyric acid (also called butyrate) and propionic acid (also called propionate). This increase is associated with a decrease in acetic acid (also called acetate) production. Butyrate production reached 40 percent after 12 hours of fermenting the microalgal dietary fiber, with 32 percent propionate and acetate as illustrated in FIGS. 9 and 10. Butyrate is used as an energy source by epithelial cells of the colon, colonocytes, and retards proliferation of malignant colonic cells.

Each SCFA plays a physiological role in the human body. Both propionate and butyrate are associated with health benefits. Histological and physiological effects of butyrate on the colon are well identified.

SCFAs are produced by fermentation of commercial dietary fiber, and mainly include acetate, propionate, and butyrate. Generally, the fermentation of commercial dietary fiber generates more acetate than propionate and less butyrate. The percentage of total acetate is over 60 percent in some cases. Butyrate is the least produced SCFA when fermenting commercial dietary fibers comprised of FOS. Generally, the most used and available commercial dietary fibers in the market are rapidly fermenting dietary fibers. Rapidly fermenting dietary fibers generate higher levels of acetate than propionate and butyrate. There is a need for dietary fibers that can generate higher levels of butyrate than what is generated by the available commercial fibers.

The ideal dietary fibers should be water-soluble, slowly fermenting, almost totally metabolized by colon microbiota, produces less gas and produces higher levels of propionate and butyrate, and promotes colon microbiota diversity with less or no side effects. This type of dietary fiber can be developed by chemical modification, but it is a costly operation.

In one embodiment of the present invention, water-soluble dietary fibers are extracted from microalgae. The novel dietary fibers have physical and chemical proprieties that make the microalgal extract a good ingredient for the food, beverages, supplement, cosmetic, animal feed and pharmaceutical industries. The water-soluble dietary fibers are easy to mix with other ingredients. The water-soluble dietary fibers have shear stress proprieties which change their viscosity under stress. The water-soluble dietary fibers can be used as an ingredient in beverages at a level of 10 to 20 percent (weight/volume) etc. Moreover, the water-soluble dietary fibers have potential health benefits, especially improving colon health.

As an example, the microalgal dietary fibers were extracted from a microalgal biomass. *Botryococcus braunii* is the microalgae strain used as a biomass source. *B. braunii* biomass was produced under phototrophic mode (light condition), heterotrophic mode (dark condition) and mixotrophic (which is both heterotrophic and phototrophic conditions). The biomass was pre-treated by starvation of the biomass. The microalgal dietary fibers were extracted by alkali hydrothermal treatment. Water soluble microalgal dietary fibers were precipitated in ethanol or calcium solution. Then the pellet was washed, pH adjusted and dried for the colon microbiota fermentation study.

The goal of the fermentation study was to examine how human colon microbiota metabolize microalgal water-soluble dietary fibers and analyze the outcome of human microbiota fermentation. The study was performed on extracted microalgal dietary fibers. It is also an opportunity to investigate any unique properties, and potential impact on health benefits and to otherwise develop nutritional and pharmaceutical applications.

Microalgal dietary fibers were mixed with human colon microbiota in the fermentation study. The study was performed for 24 hours under anaerobic conditions in order to match colonic conditions. The fermenting study period is 24 hours with sampling at 0, 6, 12 and 24 hours of the process. The main parameters evaluated in the fermentation study are Gas production, pH variation, and short chain fatty acid profile. A commercial dietary fiber, called FOS, was used as a positive control.

The microalgal dietary fibers promote the development of butyrogenic colon bacteria and significantly increase the level of butyrate production. Butyrate is one of the most important metabolites among the produced SCFA in the present disclosure. Butyrate is used as a major energy source for colonocytes, it promotes colonic epithelial tissue regeneration and proliferation, it exhibits anti-inflammatory properties, it is involved in gene expression, and it initiates apoptosis in malignant and cancer cells in the colon. Butyrate has an anti-proliferation behavior.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

The embodiments described herein provide a method for improving body health benefits especially colonic health is supported by the obtained study data. It can be more understood with the following figures.

FIG. 11 is a table description of the change in pH relative to the blank during fermentation.

Figure 1:
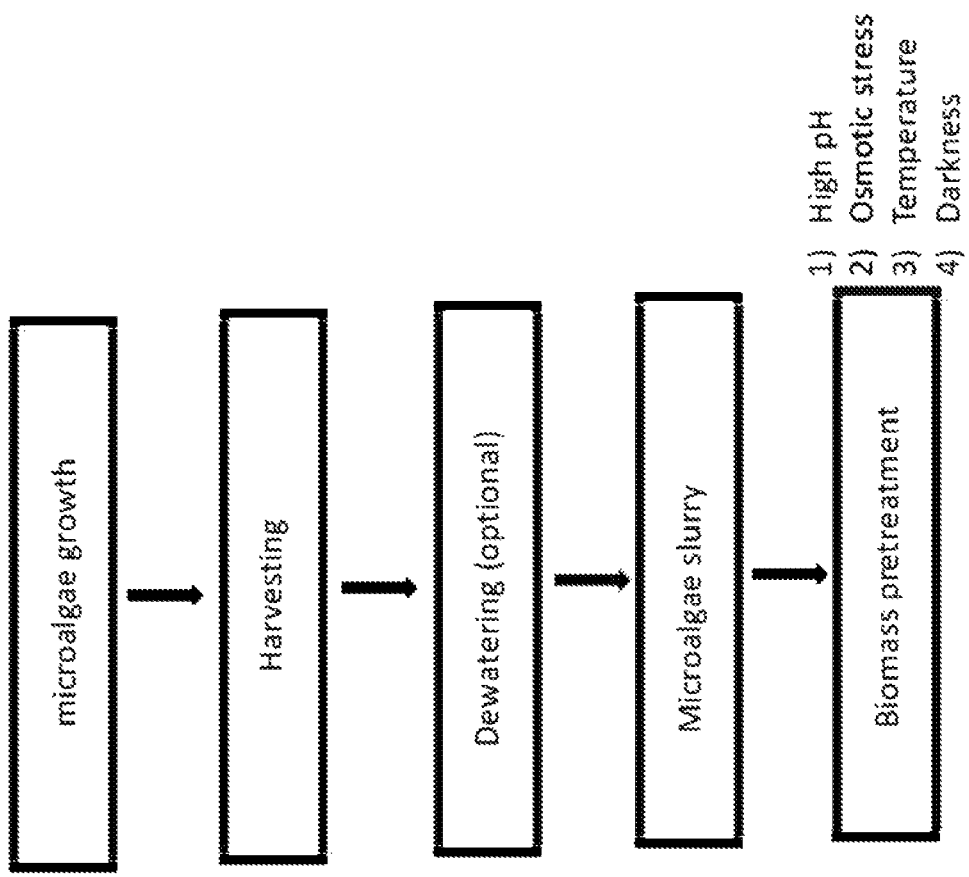
FIG. 1 illustrates the biomass production and pretreatment steps.
Figure 2:
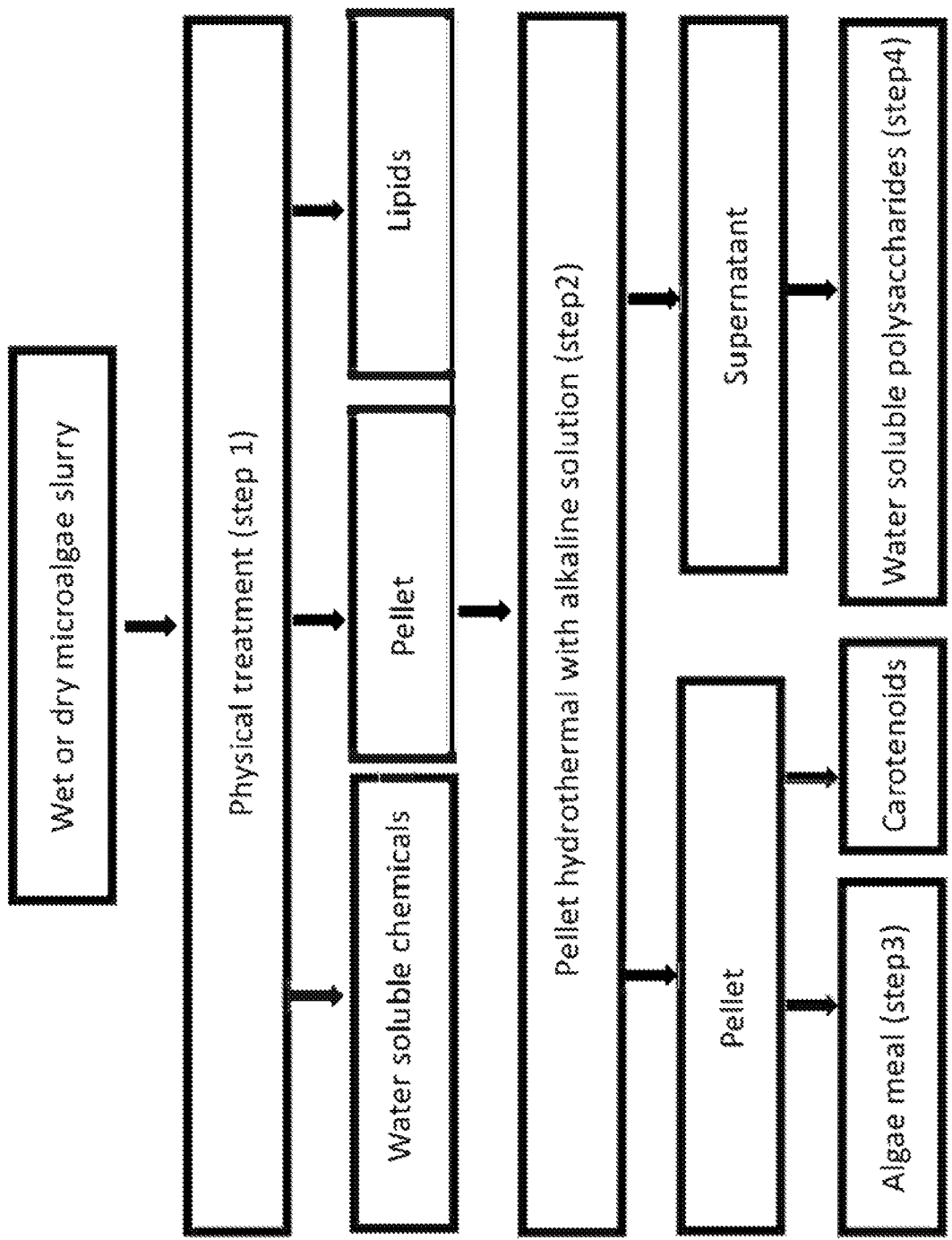
FIG. 2 illustrates a flow diagram for the processing steps in the extraction of microalgal biomass and the isolation of products.
Figure 3:
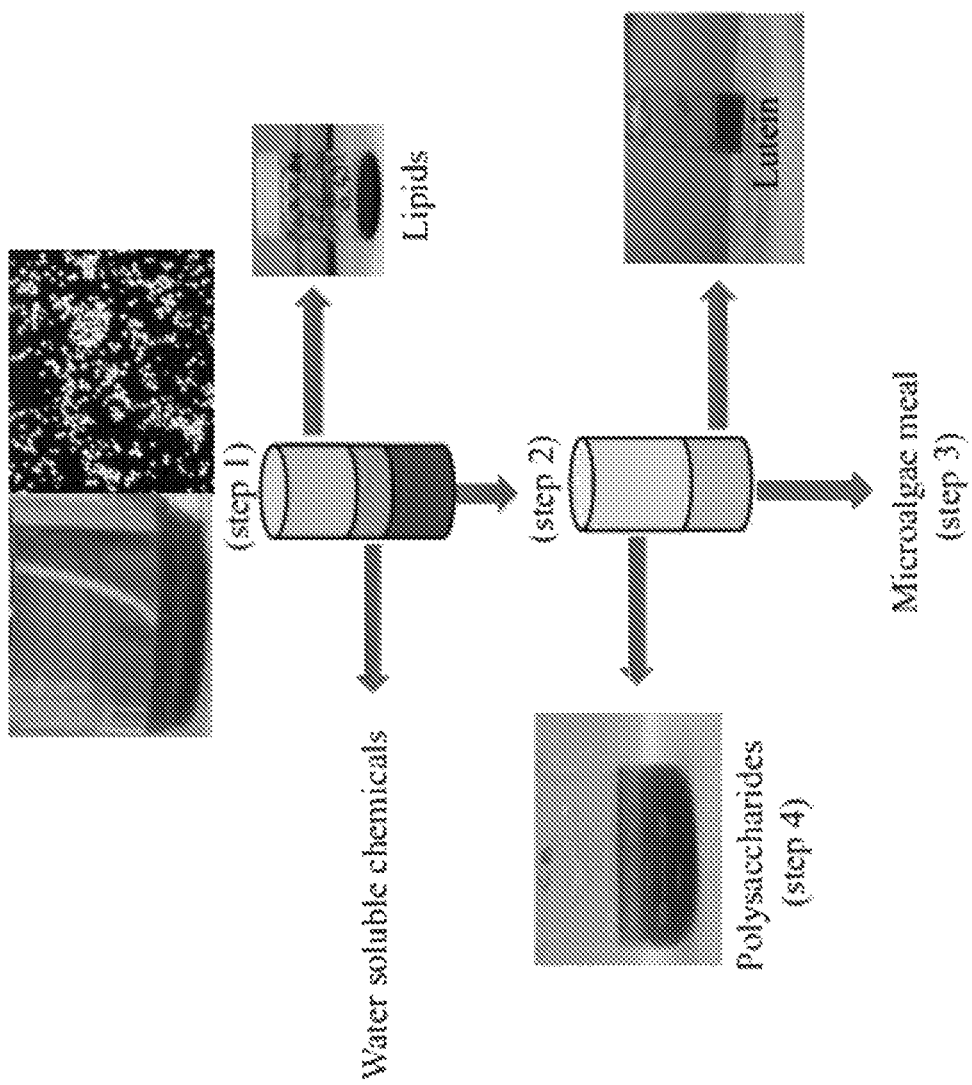
FIG. 3 illustrates the layers formed after physical treatment and the products of each layer.

Corresponding reference characters indicate corresponding parts throughout the several views. Although the drawings represent embodiments of the present disclosure, the drawings are not necessarily to scale, and certain features may be exaggerated in order to illustrate better and explain the present disclosure.

DETAILED DESCRIPTION

The embodiments disclosed below are not intended to be exhaustive or limit the disclosure to the precise forms disclosed in the following detailed description. Rather, the embodiments are chosen and described so that others skilled in the art may utilize their teachings.

The overall goal is to develop a commercially viable microalgae biorefinery using B. braunii strain. Microalgae biomass production and oil extraction costs are too high to compete with fossil fuel industry. Thus we started the research project at Purdue University by developing a new B. braunii strain. We developed the strain through a chemical mutagenesis process using an ethyl methyl sulfonate (EMS) process followed by a UV irradiation and a selection step. The selection was performed by observation of colonies with a high growth rate in darkness. Fast growing colonies were replicated and incubated in darkness and under continuous light at 25° C. Results showed that new varieties grow faster than the wild type in both darkness and continuous light. Visual observations showed that wild type strain colonies appeared after 8 days and new varieties appeared after five days of culture in darkness. Wild type colonies appeared after seven days, and new varieties appeared after five days of culture under continuous light. Colonies were larger under continuous light than in darkness. Selected strains were named B. braunii P210 and B. braunii P212.

In one embodiment, a method of extraction is a sequence of steps from biomass pre-treatment to the production of different end-products. The processing line is designed to use the same wet or dried biomass to produce high-value chemicals such as Omega-3/6/9 oil, water-soluble chemicals such as polyphenols and pigments, carotenoids, water-soluble polysaccharides and insoluble cell components called algae meal. The first step in the method is biomass starvation. The second step is a physical treatment to extract oil and water-soluble chemicals such as polyphenols. The third step is a hydrothermal treatment of the residual biomass with adjusted pH value to extract carotenoids and polysaccharides. The fourth step is the precipitation of the water-soluble polysaccharide in the supernatant using either calcium or alcohol solution. The fifth step is a solvent extraction of carotenoids from the pellet using hexanes. At the end, the water insoluble fraction (leftover) is designated to be used as animal feed.

The method is a one-line processing technology; it is a way to improve the feasibility of a commercial biorefinery. The water-soluble polysaccharides, with relatively low viscosity at low shear stress, are produced with the one-line processing method have specific physical properties and many commercial applications. For example, the water-soluble polysaccharides with relatively, low viscosity at low shear stress are used in food & beverages, cosmetic, and nutraceuticals industries.

Biomass Production

BG11 culture medium was used to grow B. braunii strains under different growth conditions. 500 mL Flasks were used for biomass growth. Inoculated flasks were incubated in a shaker with a rotation 100 rpm at 25° C. Two growth modes were used including darkness and continuous light. The continuous light mode was performed in the presence of organic carbon or phototrophic condition. The organic carbon was a combination of glycerol and glucose. The used glycerol was obtained from a biodiesel plant. Sugar or molasses can also be used as carbon source. Sugar may also be a granulated commercial sugar from the super market. Non-purified molasses is an industrial waste and may also be used as the organic carbon component. The dose of organic carbon is about 2 to about 20 g/L, particularly about 2 g/L to about 5 g/L.

The biomass growth cycle was 6 days. A harvesting process was performed on the 7$^{th}$ day by centrifugation at 2000 rpm for 5 min. The supernatant was discarded, and the pellet was washed twice with purified water.

Results showed that strains grown in darkness yielded 1.03, 1.95 and 1.74 g/L dry weight with wild *B. braunii*, *B. braunii* P210 and *B. braunii* P212 respectively and confirmed the selection results of mutants. Under continuous light, wild *B. braunii*, *B. braunii* P210 and *B. braunii* P212 yielded 2.08, 4.05 and 3.75 g/L (dw) respectively.

Pre-treatment of harvested biomass was performed using 0.5 g/L sodium nitrate and osmotic stress, NaCl 10 mM, during high growth at pH 9 in darkness for 3 days. The post-harvest treatment of the concentrated biomass is optional, and the type of post-treatment depends on the response of each microalgae strain. Post-treatment is generally performed to improve the yield of cell components such as oil and carotenoids, and to soften the cell wall for next processing steps.

The treatments can also be nutrient starvation. In one embodiment, nitrogen starvation is used. The nitrogen concentration may be about 0 g/L to about 1.5 g/L, about 0.03 g/L to about 0.5 g/L, particularly about 0.05 g/L to about 0.2 g/L.

The pH is another parameter that can be used to initiate a stress condition and soften the cell wall. High pH is used to liberate carotenoids. The pH is about 7 to about 10, about pH 8 to about pH 9.5, particularly about pH 8 to about pH 9.

Darkness is used to starve microalgae cells from light and photosynthesis. Under darkness microalgae cells cannot utilize solar energy to convert $CO_2$ into organic molecules and energy. Metabolism during darkness initiates fermentation process and consumes oxygen. In this regard, oxygenated air is provided to the slurry. Under these conditions, cells use stored molecules or polymers, such as carbohydrates, as energy sources and intermediary metabolites. Darkness is a form of physiologic stress that induces microalgae cells to accelerate the accumulation of oil, and carotenoids to avoid oxidative stress.

Osmotic stress is another way to change the metabolic response of cells biomass. Sodium chloride (NaCl) is the most used osmolyte for freshwater strains. The osmotic stress is about 0.5 mM to about 200 mM NaCl, about 5 mM to about 100 mM, particularly about 5 mM to about 50 mM.

The slurry may contain a microalgae concentration about 0.5 g/L to about 90 g/L dry weight, about 5 g/L to about 80 g/L, particularly about 30 g/L to about 70 g/L.

The temperature of starvation treatment is about 18° C. to about 32° C., about 20° C. to about 25° C.

Filamentous and unicellular microalgae biomasses may include the following genera: *Botryococcus, Chlorella, Skeletonema, Thalassiosira, Phaeodactylum, Chaetoceros, Cylindrotheca, Euglena, Bellerochea, Actinocyclus, nitzchia, Cyclotella, Isochrysis, Pseudoisochrysis, Dicrateria, Monochrysis, Tetraselmis, Pyramimonas, Micromonas, Chroomonas, Cryptomonas, Rhodomonas, Chlamydomonas, Olisthodiscus, Carteria, Dunaliella, Spirulina* and *Nannochloropsis*.

Oil Extraction and Fatty Acid Analysis

Total lipid extraction was performed using Folch and Stanley procedure (1957) for further fatty acid analysis. Folch and Stanley procedure is generally performed at the laboratory scale. It is a way to develop a whole picture on the fatty acid profile because it includes total, polar, and neutral lipids. The present methods are focused on neutral lipids. However, further information on polar lipids can generate information on more commercial products.

Results show that wild *B. braunii*, *B. braunii* P210 and *B. braunii* P212 yielded 20%, 42% and 35% of the dry weight respectively. Neutral lipids are a potential source of biofuels. *B. braunii* P210 accumulated more neutral lipids at 85.1% than the wild type at 70.9%. In contrast, *B. braunii* P210 contained the lowest amount of polar lipids at 14.8%, *B. braunii* P210 contained 18.48%, and the wild type contained 29%. Wild type accumulated higher levels of unsaturated fatty acids (73.59%) than *B. braunii* P210 (67.64%) and P212 (66.35%) varieties. *B. braunii* P210 and P212 are distinguishable from the wild type in growth rate and neutral lipids accumulation. *B. braunii* P210 showed its potential to grow under phototrophic, heterotrophic and mixotrophic conditions. The mutant can use both $CO_2$ and organic compound as a carbon source. The highest growth rate was obtained under mixotrophic mode. SCFAs analysis shows that the strain *B. braunii* P210 accumulated more palmitic, stearic and oleic acid than *B. braunii* P2012 and the wild type. 35% of palmitic acid, 15% of stearic acid and 19.69% of oleic acid among neutral lipids accumulated in *B. braunii* P210.

Step 1: Physical Pre-Treatment

The method for the extraction of oil and water-soluble chemicals or any other cell components begins with a physical pre-treatment. This step involves a disruptive process to disintegrate the membranes and organelles. This step can be performed using many types of physical treatments. It may be an advanced homogenization process of the biomass to allow chemicals to escape cell organelles. Physical treatments include grinding, ultra-sonication, extruding, microfluidization, etc.

Ultra-sonication was performed on pretreated and non-pretreated harvested biomass. Results show that post-harvest treatment improved neutral oil yield. The yield was increased about 10% to about 15%. The combination of ultra-sonication with a solvent, such as hexane, improved oil yield. The yield was increased about 25% comparatively to non-treated post-harvest biomass. Similar results were obtained by combining ultra-sonication and extrusion. Centrifugation was performed to separate the 3 types of cell components including oil on the top, water-soluble chemicals, and the pellet in the bottom. The centrifugation was performed at a speed of about 500 rpm to about 15000 rpm, about 1000 rpm to about 10000 rpm particularly about 2000 rpm to about 5000 rpm.

SCFAs profile shows that neutral lipids extract from *B. braunii* P2010 can be used as a source of biofuels. Moreover, there is an opportunity to use it as a food ingredient or in cosmetic industry due to the content of omega-3/6/9 in the extract.

Step 2: Water Soluble Chemicals Extraction

Water soluble chemicals extraction is the second step of the processing line. This step can be performed using a variety of physical treatments. After oil extraction by a combination of ultra-sonication and hexane, the pellet was optionally mixed by adding 5% to about 15% water (volume/pellet weight). Ultra-sonication was optionally performed again followed by centrifugation. The repeated Ultra-sonication depends on the biomass homogenization efficiency. The biomass already contains up to 80% water. It could contain enough water for a supernatant containing water soluble chemicals. The water-soluble fraction, consisting mainly of phenolic compounds and other pigments, was separated from the pellet. This pellet was used in the hydro-thermal treatment step.

Step 3: Hydrothermal Treatment

Hydro-thermal treatment was performed on the pellet using an aqueous solution (2M KOH and 2 M NaOH). The suspension was held at 70° C. for 12 hours with stirring. The temperature and period of heating depend on the soluble polysaccharides yield. The mix was centrifuged at 4000 rpm for 15 min. The supernatant was used to precipitate water-soluble polysaccharides and the pellet to extract carotenoids.

The hydrothermal treatment may be performed using 120° C. and high pressure, for example autoclave or pressure cooker, for about 5 min to about 60 min, particularly about 20 min to about 30 min. The hydrothermal treatment may be performed at a temperature about 60° C. to about 120° C., particularly about 80° C. to about 100° C. The hydrothermal treatment is about 10 min to about 24 hours, particularly about 60 min to about 12 hours.

The high pH water solution comprises NaOH and KOH at the concentration about 0.5 M to about 4M, 1 M to about 2M each. The high pH water solution comprises NaOH/KOH; the molar ratio is about 0:4 to about 4:0, 1:3 to about 3:1, particularly 2:2 to about 2:2. The ratio of solid biomass/solution is about 1:1 to about 100:1, about 5:1 to about 50:1, particularly about 10:1 to about 20:1. The solution of a base may be selected from the group consisting of sodium hydroxide, potassium hydroxide, calcium hydroxide, alkali metals, alkaline earth metals, Ammonium hydroxide, ammonia, sodium carbonate, potassium carbonate, boron hydroxide, aluminum hydroxide, borax, amino alcohols such as ethanolamine, diethanolamine, Triethanolamine, isopropanolamine, diisopropylamine, triisopropylamine, propylamine, 2-propylamine, methylamine, dimethylamine, trimethylamine, dimethylethanolamine, monoethylethanolamine, 2-(2-aminoethoxy) ethanol, diglycolamines, diethylamine and a mixtures thereof.

Step 4: Carotenoid Extraction and Analysis

After hydrothermal treatment and centrifugation, the pellet is used to extract carotenoids. Carotenoids are water insoluble pigments and should be extracted by solvents. The solvent can be oil or chemical solvents. Oil includes olive oil or any vegetable oil. The chemical solvent can be hexane, acetone, ethanol, isopropanol, etc. The use of solvents may be a single solvent or a combination to improve the yield.

Example 1: Carotenoid extraction was performed on pellet as follows: 5 volumes of hexane was gently mixed with the pellet at the ratio of 5/1 (v/w). Hexane with carotenoids floated to the surface. The supernatant is collected. The hexane wash was repeated until the supernatant is clear. All of the solvent extracts are collected and then evaporated at 50° C. in a rotary evaporator. The pH of the extracted carotenoids pellet is adjusted to 7 and washed with distilled water, and then dried. The yield was estimated by weight.

A reverse phase HPLC system (Agilent Instruments) interfaced with LC-MS (Agilent Mass Spectrometer) was used to analyze hexane carotenoid extracts at the Purdue University facility. A C18 HPLC column was used for the chromatographic separation. The mobile phase is a buffer solution (pH 3.6) in methanol (70/30%) at a flow rate 0.4 mL/min. Carotenoid components were identified and quantified from their peak areas in relation to the respective reference standards.

The effect of processing on trans-cis isomerization of carotenoids was investigated by Marx et al. (2003). Marx reported that there is an effect of heat processing on beta-carotene isomerization process relative to the raw carrot. However, this rate is higher with bleaching at 130° C. than at 121° C. Analysis results showed that the percentage of cis-isomers was increased with this type of treatment.

Figure 4:
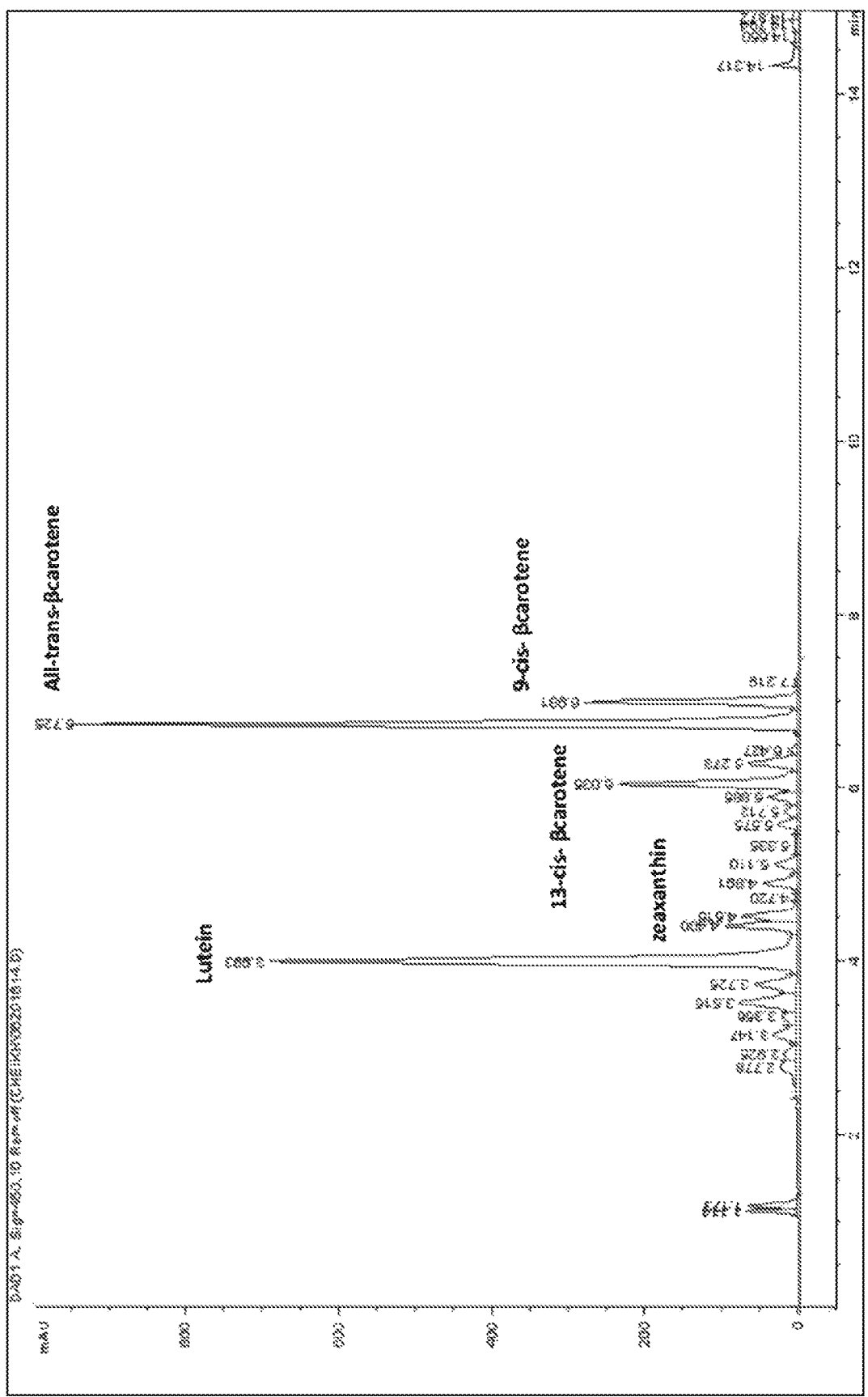
FIG. 4 illustrates a chromatogram from the analysis of the solvent extract profile from the pellet in FIG. 2.

Hexane extract analysis showed that lutein is a major carotenoid component in the extract (FIG. 4). FIG. 4 shows that there a slight effect of the hydrothermic treatment applied in this step. There is no observed Cis-isomerization of lutein. There is only 9- and 13-cis-βcarotene respectively 5% and 8%. Many health benefits have been reported to be associated with lutein. It was demonstrated that lutein possesses antioxidant properties (Sies et al., 1992). Lutein also modulates the immune system with anti-inflammatory effects (Moraes et al., 2015). Sindhu et al. (2010) reported that lutein scavenges superoxide radicals, hydroxyl radicals and inhibits in vitro lipids peroxidation.

Production of Algae Meal

Carotenoids extraction is optional. This step may be removed from the process, and the pellet is directly used as algae meal. In both cases, the pellet is washed and pH adjusted before it is used as algae meal.

Step 5: Water Soluble Polysaccharides Extraction

Polysaccharides Precipitation:

Based on solubility, there are two types of polysaccharides: water-soluble and water-insoluble fiber. The water-soluble polysaccharides are targeted in the supernatant. The supernatant was obtained after centrifugation of hydrothermal treatment of the pellet. The supernatant is comprising the water-soluble polysaccharide maybe used as a product after pH adjustment. The second alternative is harvesting by evaporation. Evaporation may proceed after pH adjustment. The evaporation process is performed and then stopped when a targeted level of product moisture is obtained. Harvesting by precipitation may be performed using an agent that forms a liaison with the fiber to increase density and initiate precipitation. The agent can be alcohol like ethanol, isopropanol, etc. Ions are another type of agent that forms complexes and then precipitates. Calcium is the most used ionic precipitation agent for polyanionic polymers.

Water-soluble fibers in the supernatant were precipitated using calcium chloride $CaCl_2$ (5%) or ethanol at 70% dilution in water. Instant precipitation is initiated. After 30 min, the supernatant was removed, and the pellet was recovered. Calcium precipitation may be performed using a calcium concentration about 2% to about 40% (weight/volume), about 5% to about 20%, particularly about 5% to about 10%. Ethanol dilution is ranging from about 45% to about 100%, particularly from about 60% to about 80%.

The pellet was gently washed at pH 2.5 and then dried for further analysis. Fifty mL of purified water is added to the precipitated fiber, then the pH is adjusted to 2.5 as a washing step. The pellet is then gently mixed for 15 min and then centrifuged for 15 min at 4000 rpm. This step is repeated twice, or more if needed to free the pellet from calcium. The washing pH may be about pH 1 to pH 6, and about pH 2 to pH 4, particularly about pH 2 to about pH 3, in cases where only water is used in the washing step. If a precipitation solvent is used such as ethanol, the pH may be about pH 1 to about pH 14, pH 2 to about pH 10, particularly pH 2 to about pH 7.

The pH of the pellet is then adjusted based on the commercial application. Generally, the pH is adjusted to neutral pH. Polysaccharides may be used in the liquid or dried form. In the case of a dried form, the drying step is performed at a different range of temperature. The temperature is about 20° C. to about 100° C., about 30° C. to about 70° C., particularly about 35° C. to about 42° C. The drying step may be performed using equipment such as an oven, a convection oven, in the air, under sun light, freeze dryer, etc.

The period of drying may be extended till the sample will reach the targeted moisture. Results show that water-soluble yield reached 28% of total biomass.

Monosaccharide and Glycosyl-Linkage Composition

Monosaccharide and galacturonic acid analyses are performed as described by Somerville et al., 2004. Structural features of fiber samples are analyzed as described by Somerville et al., 2004. The concentration of uronic acids is performed by using the carbazole-sulfuric acid method and measuring the total content as glucuronic acid for the absorbance at 530 nm (U-2001 spectrophotometer Hitachi Ltd.).

Results show that *botroyococcus braunii* P210 is composed mainly of galactose, rhamose, glucose, arabinose and uronic acid, and suggests no sulfuric acid. The monosaccharide composition is 32% mol % galactose, 23.72 mol % rhamose, 16.38 mol % glucose, 7.45 mol % arabinose, 6.16 mol % xylose, and 3.4 mol % manose.

Analysis of Linkage Ratio by Proton Nuclear Magnetic Resonance (H NMR)

Spectroscopy was performed to determine the relative abundance of α-1,4 and α-1,6 linkages in water-soluble polysaccharides using Varian Unity Inova 300 MHz, Varian INC., Palo Alto, Calif.). The RMN study of glycosyl-linkage analysis showed that the polymers are less branched and dominated by beta (1-4) linkage.

Physical Properties of Polysaccharides

Polysaccharides are mostly used in the food and beverages industry. Industry uses the physical properties of polysaccharides to vary texture and quality of food products. Polysaccharides may be used as stabilizing, dispersing, thickening, and gelling agents. They are involved in cooking, processing, and manufacturing. Products comprising polysaccharides show some deformation behaviors like elongation, shear stress, and pressure. The shear stress is the result of a force applied on the surface divided by surface area occupied by the tested element. It is a friction between the fluid components. Rheological studies of water-soluble polysaccharides in the present invention will generate data to elucidate the role of their structure and potential functionalities.

The microalgae polysaccharides physical properties analysis is a way to investigate the potential applications, and how to overcome future plant and macroalgae polysaccharides shortages in functional food & beverages, pharmaceuticals and supplements.

Generally, polysaccharides rheology study provides helpful information in processing, formulation, quality control analysis, and product texture. Water soluble polysaccharides structure, stability at different pH, temperature, shear stress, and viscosity at different concentrations are parameters generally investigated to characterize polysaccharides. It has been reported that functional properties of polysaccharides are directly related to their structure (Percival, 1979).

Viscosities of fiber solutions samples were measured using a rotational rheometer (AR-G2 model, TA Instruments, Newcastle, Del., USA) using a parallel-plate geometry (diameter 20-mm) and a 500 μm gap at 25° C. A shear rate range of 0.01 to 150 $s^{-1}$ was used. The viscosity behavior of the novel fiber was measured at 25° C. as described by Lin et al. (2015). The concentration of the fiber in water was 10% (w/v).

Figure 5:
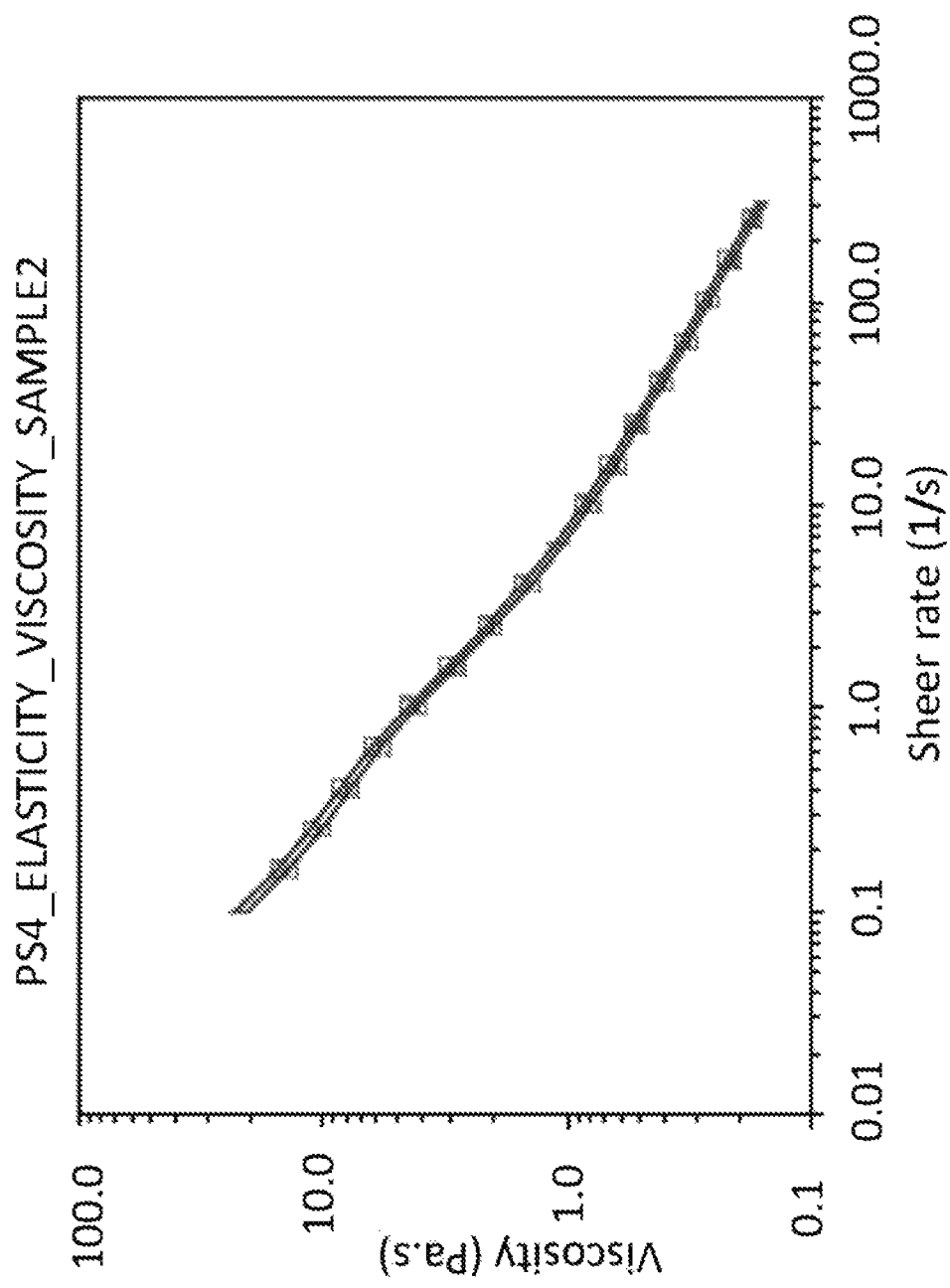
FIG. 5 illustrates a rheogram of Sample 2 of microalgal water-soluble fiber (MWSF).

The profile of viscosity versus shear rate is shown in FIG. 5. The steady shear measurements of the 10% solution indicated a decrease of viscosity associated with an increase in shear stress. The fiber sample showed a non-Newtonian pseudo-elastic viscosity. It is a shear thinning behavior in the shear rate range of 0.01 to 1000 $s^{-1}$. The decreasing viscosity and increasing shear rate behavior is an indication of the physical structure of the microalgal water-soluble polysaccharide. This property indicates alignment of the less branched polysaccharide polymer in the direction of the flow under increasing shear rate as demonstrated above by the Proton Nuclear Magnetic Resonance study. The fiber solution (10%) flow behavior showed a pseudoplastic, non-Newtonian fluid without yield stress.

The high viscosity at low shear contributes to the formation of an extended hydrogel matrix. In the present case, there is no formation of hydrogel at 10% concentration. An increase of the microalgal water-soluble concentration will generate the formation of a hydrogel. For the formation of fluid, 10% to 20% is the right concentration range. The concentration may be less than 10% or higher than 20% based on the purpose of the fluid.

Figure 6:
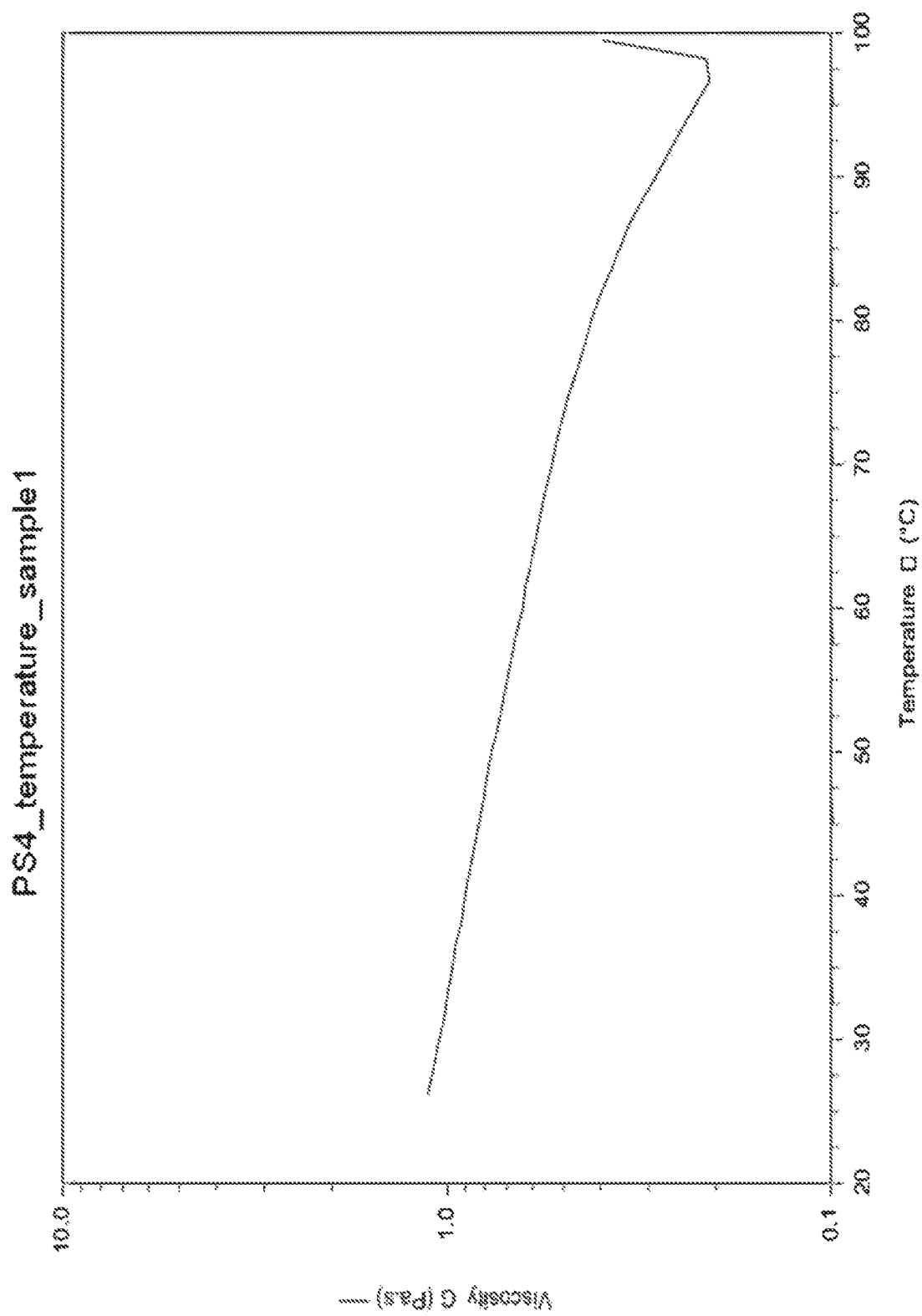
FIG. 6 illustrates the change in viscosity of MWSF in response to changes in temperature.

Microalgal water-soluble polysaccharides as ingredients in a system may influence the physical properties, especially viscosity and other rheological parameters. Many biopolymers, like xanthan, demonstrate stable viscous behavior vs temperature (Naji et al., 2012). Viscosity test was performed on the polysaccharide solution at a temperature range from 25° C. to 100° C. to investigate the influence of the temperature. Results show a decreasing viscosity with increasing temperature (FIG. 6). This is an indication that the microalgal water-soluble polysaccharides rheology property in solution is temperature dependent. This property can be used during the processing for an easy ingredient mixing with the microalgal water-soluble polysaccharides.

The viscosity of the polysaccharide solution was dramatically influenced by an increase in temperature. This property provides a high flow behavior index at warm to high temperature, especially at a low shear rate, so that a decrease was observed with increasing temperature. However, the viscosity increased to 0.2 Pas at 95° C. (FIG. 6). The concentration of the polysaccharides increases due to water evaporation, and creates hydrophobic interactions, resulting in viscosity increase.

The relatively low viscosity at low shear stress, high shear thinning, and water solubility properties of the novel fiber show potential application in pharmaceutical, cosmetics, food, and beverages fields. The high shear thinning property is used for an easy pump processing of liquid foods comprising microalgal water-soluble polysaccharides. The high sheet thinning property allows for a thinner consistency of liquid food during swallowing (Stokes et al., 2013). It had been reported that many hydrocolloids show a correlation between high shear thinning with a lower degree of slimness in the mouth (Yaseen et al., 2005). The rheology properties exhibited by the microalgal water-soluble polysaccharides show that they may provide an even better mouthfeel. They may be easy to mix with other ingredients. Since they are water-soluble polysaccharides, they may be used as beverage ingredients to develop a desired liquid physical property and make it a functional (healthy) product.

The ratio of polysaccharides to a product may be about 0.1:10 to about 9.99:10, about 1:10 to about 7:10, about 2:10 to about 5:10. This ratio depends on the product target. A lower ratio from about 0.1:10 to about 4:10, from about 1:10 to about 3:10, particularly from about 2:10 to about 3:10 is recommended for beverages production. This ratio will provide the product a slimness and mouth feeling during swallowing.

The viscosity change based on the heating temperature is another desired property for different commercial applications such as food, cosmetic and beverages. Processing at high temperature allows microalgal water-soluble polysaccharides to be easily mixed with other ingredients and facilitates flow and pumping during processing.

Microalgal water-soluble polysaccharides may be used as an ingredient in cosmetics and food industry due to the shear thinning property. Microalgal water-soluble polysaccharides may be used in personal care products to develop the desired rheology. Microalgal water-soluble polysaccharides may enable viscosity modification with silky and smooth texture and homogenous dispersion of other ingredients. Since they are water-soluble, the cosmetic product can be washed out when the user decided to do so. Other ingredients may be lipids or any other synthetic or biosynthetic chemical. Personnel care products include for example lotion, cream, and lipstick.

***Water Soluble Polysaccharides Fermentation Study

The colon bacteria fermentation study showed that compared to commercially dietary fiber FOS, the microalgal dietary water-soluble fibers (called prebiotics) are slower fermenting polysaccharides. Fermentation of microalgal dietary fibers by colonic microbiota generated twice the volume of butyrate than acetate (See FIG. 10). The butyrate ratio is higher with microalgal dietary water-soluble fibers than with FOS. Butyrate is known for its capability to improve colonic health, promote epithelial cells proliferation of the colon and prevent colon cancer by inhibiting malignant cells proliferation. Moreover, less gas volume was generated during fermentation of microalgal dietary fibers than with FOS. Less gas production is analogous to preventing consumer bloating and discomfort.

Microalgae is a sustainable biomass source and can complement land crops in the base of the food chain. Microalgae is an alternative feedstock to produce many end products associated with human health benefits, and products used in food, beverages, supplements, cosmetic, animal feed, pharmaceuticals, bioenergy, etc.

Microalgae is a micro crop with many advantages such as the potential to convert $CO_2$ in the presence of solar energy into organic molecules and energy, grow in seawater, or on land where no land crop can grow, use recycled water, and yearly produce biomass at a yield 50 times higher than with land crop. Microalgae is a unique aquatic micro-crop which can provide unique products with unique characteristics. The present invention describes microalgal water-soluble dietary fiber and a method for improving colon health.

The microalgae biomass strain is obtained from *B. braunii* growth. It can be produced under phototrophic, heterotrophic or photo-heterotrophic modes. The mineral source for the microalgae biomass growth is the culture medium BG11, including nitrogen, macroelements and microelements. $CO_2$ was provided by air bubbling (2 percent) in 6 L flasks. The growth was performed under continuous light. Biomass was harvested and concentrated for a pre-treatment step. The pre-treatment was performed by nitrogen starvation with osmotic shock in darkness. The pre-treatment residency may be about 12 hours to about 120 hours, particularly about 24 hours to about 72 hours. Oxygen was provided by air bubbling.

The concentrated pre-treated biomass was used for fiber extraction and other high value chemicals. The biomass can be used as wet biomass or dry. The biomass may be dried in a convection oven, in the air or by freeze drying. Drying is beneficial if there is a break in processing and an intermediate storage step is required. The biomass processing is described herein under the section titled "biomass processing for high-value chemicals production." The extraction was performed by an alkali hydrothermal treatment. The supernatant was collected for the microalgal water-soluble dietary fibers precipitation. The precipitation was performed using 70 percent ethanol. The pellet was washed and pH was adjusted to about pH 7, and then dried. The drying process can be proceeded in an oven, or using air or freeze drying. The oven can be a convection oven at temperature about 30° C. to about 100° C., about 40° C. to about 65° C. Particularly, it is about 42° C. in a convection oven. The dried microalgal water-soluble dietary fiber will be used to study their fermenting behavior and if they are associated with any health benefits. The microalgal water-soluble dietary fiber may be dried using the freeze-drying method. The drying process may also be conducted for example by freeze drying, heating in an oven, or by air. Microalgal water-soluble polysaccharides can be used alone or mixed with other ingredients such as other dietary fibers. Dried fibers are used for fermentation study.

Microalgae used for water-soluble polysaccharides extraction may be a Chlorophyceae. Preferably is among genus *Botryococcus, Chlorella, Skeletonema, Thalassiosira, Phaeodactylum, Chaetoceros, Cylindrotheca, Euglena, Bellerochea, Actinocyclus, Nitzchia, Cyclotella, Isochrysis, Pseudoisochrysis, Dicrateria, Monochrysis, Tetraselmis, Pyramimonas, Micromonas, Chroomonas, Cryptomonas, Rhodomonas, Haematococcus, Chlamydomonas, Olisthodiscus, Carteria, Dunaliella, Spirulina* and *Nannochloropsis.*

Example 1

In Vitro Human Fecal Batch Fermentation Analysis

In vitro fecal batch fermentation was performed according to the method reported by Rose et al. (2010). FOS from Orafti (Tienen, Belgium) was used as a control. A carbonate-phosphate buffer was prepared and immediately saturated by sterile bubbling $CO_2$. A sterile cysteine hydrochloride solution (0.1 g/mL) was added (2.5 mL/L buffer). Fecal samples were obtained from three healthy volunteers who have not taken antibiotics for at least three months and have consumed their routine diets. The feces were pooled and prepared following the method of Rose et al. (2010). Test tubes with no substrate will be used as blanks at each sampling period. After 6, 12, and 24 hours of fermentation, assigned tubes will be removed from the water bath, and total gas volume will be measured using a syringe. SCFA content will be quantified as described by Karppinen (2000).

The in vitro fermentation test of the microalgal fiber was performed. The in vitro fecal fermentation was carried as described by Rose et al. (2010). The experiment plot includes a blank and FOS as a positive control. The study measured total gas production, the ratio of SCFAs and pH variation during the fermentation experiment. SCFAs mainly include acetate, propionate and butyrate. Gas generation is a sign of fermentation in the large intestine. The volume of total gas is a parameter used to determine the fermenting behavior of the microalgal dietary fiber by the colon microbiota. The SCFAs profile is used to determine potential physiological effects in the human body.

A high gas volume creates undesirable side effects such as flatulence, bloating, and eructation (Vulevic, et al., 2015). It creates discomfort for the consumer. The intensity of the discomfort depends on the nature and concentration of the dietary fiber. Diarrhea symptoms were also reported in some cases with rapidly fermented dietary fibers. It has been reported that rapidly fermented fiber such as FOS is associated with high gas volume generation in the large intestine during the first hours of fermentation (Lu et al., 2017). A daily intake equal or over 7 g/day of FOS can be associated with diarrhea symptoms. Other studies showed that FOS, resistant potato starch, and psyllium fermentation generate the most gas in the first four hours (Lovino et al., 2014).

Additional embodiments described herein provide a method for improving health benefits and colon health, especially bowel health. This improvement is supported by the fermentation study described herein comparing the microalgal water-soluble dietary fibers to commercially available dietary fibers in the market, i.e., FOS. The embodiments include: 1) a composition comprising a slowly fermenting microalgal water-soluble dietary fibers product when metabolized by colon microbiota, 2) less gas production by fermenting microalgal water-soluble dietary fibers than FOS, 3) production of higher levels of propionate, 4) the microalgal water-soluble dietary fibers are butyrogenic in that their fermenting process is associated with high level of butyrate, 5) production of a low level of acetate, and 6) there is less pH variation during the fermenting process of microalgal water-soluble dietary fibers.

Figure 7:
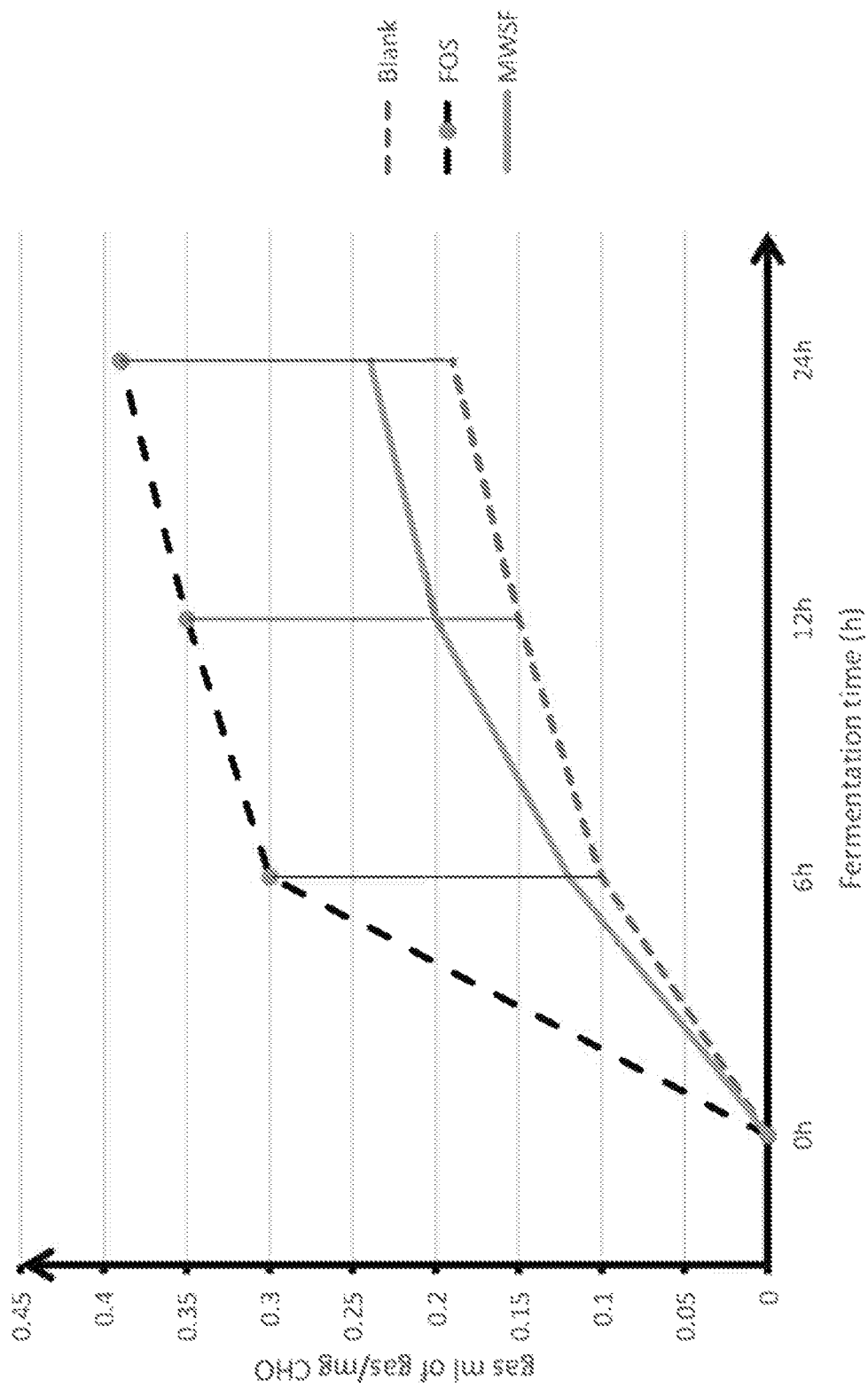
FIG. 7 is a schematic description of the volume of gas produced by fermenting a blank as a negative control, the fructoolisaccharides (FOS) reference as a positive control, and the sample MWSF.

As illustrated in FIG. 7, generated gas data demonstrate that the colon microbiota metabolized the microalgal dietary fiber as substrate. FOS fermentation generates three times the volume of gas in the first six hours than with the microalgal water-soluble dietary fiber as shown in FIG. 7. Gas volume results from the fermentation of FOS confirms previously reported data.

A slowly fermenting behavior was observed with microalgal water-soluble dietary fibers comparatively to the rapidly fermenting dietary fibers (FOS). As illustrated in FIG. 7, Data showed that fermenting microalgal water-soluble dietary fibers generate less gas volume than FOS. In the first 6 hours of the fermentation, 0.3 mL gas/mg was generated by FOS, and 0.12 mL gas/mg by microalgal water-soluble dietary fiber. Fermentation of the microalgal water-soluble dietary fiber resulted in a gradual increase in the production of gas during the 24 hour test period. Fermentation of the reference, FOS, resulted in a rapid production of gas, 0.3 mL/mg in the first 6 hours. The high initial production rate shown by FOS may create a consumer bloating and discomfort comparatively to microalgal water-soluble dietary fiber.

As reported above, side effects of high gas volume generated by rapidly fermented dietary fibers such as FOS are boating, discomfort and diarrhea symptoms. The novelty with the dietary fiber disclosed herein is the low gas volume production, which will avoid side effects like those observed with FOS consumption. The fermentation rate of dietary fiber is an important factor. Low gas with gradual volume production is found in the slowly fermentating microalgal fiber experiment, as shown in FIG. 7. Furthermore, fermentation of the microalgal fiber produces gas all along the colon, in both proximal and distal regions.

Figure 8:
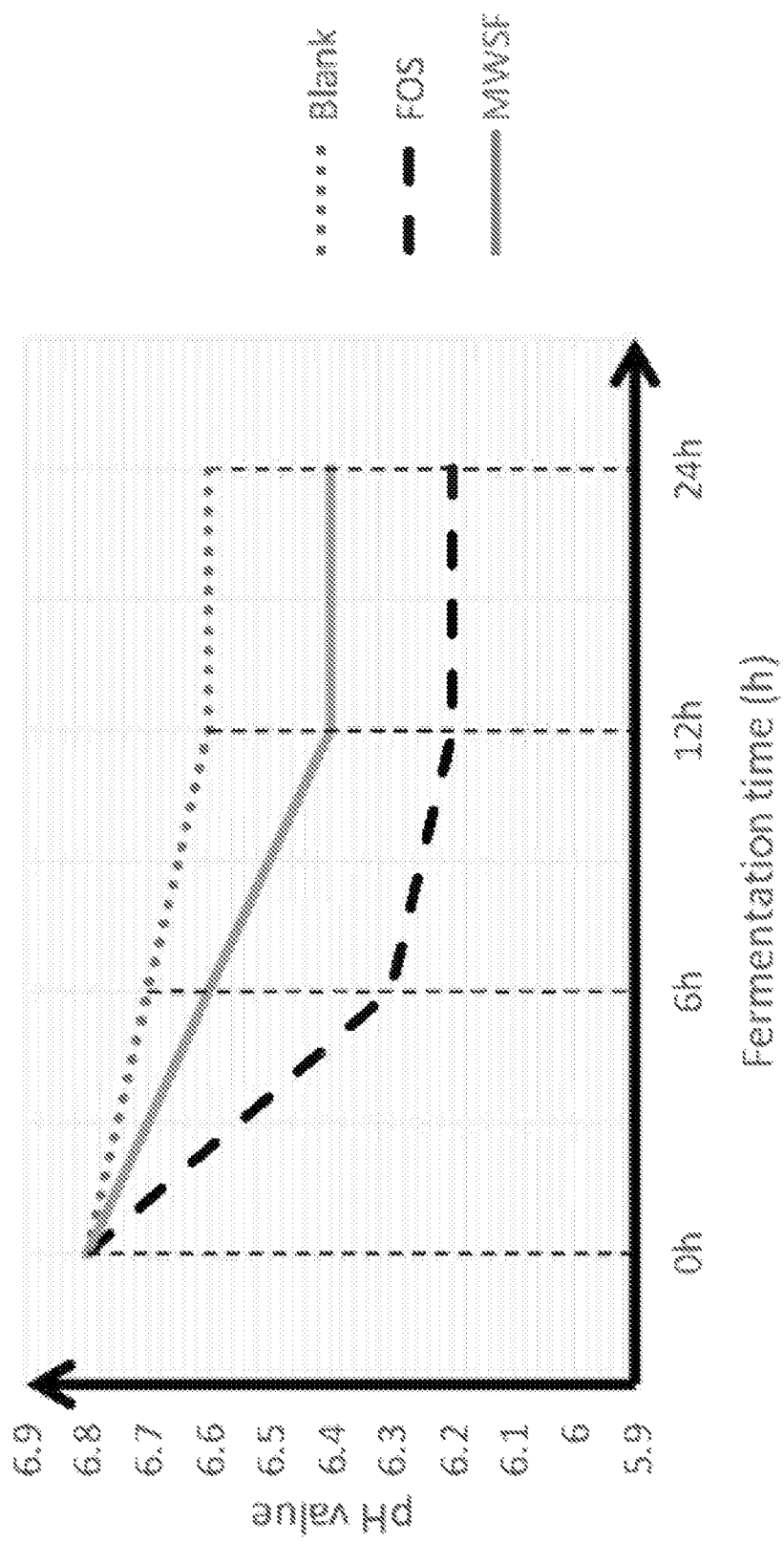
FIG. 8 is a schematic description of the change in pH during fermentation of a blank as a negative control, the FOS reference as a positive control, and the sample MWSF.

As illustrated in FIG. 8, a slight pH variation was observed during the fermentation of the fiber composition than with FOS. The slow fermentation of microalgal fiber is a progressive SCFA generating process, which it does not result in a pH drop. The pH variation can influence epithelial transport. The pH dropped by 6 with FOS and by 2 with microalgal water-soluble dietary fiber in the first 6 hours of the fermentation process. Table 1 shows the change in pH relative to the blank, which is higher with fermenting FOS than the microalgal water-soluble dietary fiber.

As illustrated in FIG. 8, fermentation of microalgal water-soluble dietary fiber showed less pH variation during the 24 hour study comparative to the fermentation of FOS. Again, the fermenting microalgal water-soluble dietary fiber displayed a gradual pH decrease. In contrast, FOS fermentation was associated with a pH drop in the first 6 hours.

The composition of Gut (colon) microbiota depends on many factors including diet, genetic, obesity, etc. Diets rich in dietary fiber dramatically alter the gut microbiota based on the nature of the fiber. Short chain fatty acids produced by fermentation of gut microbiota have been reported to influence the intestinal and hepatic metabolism (Parnell et al., 2012). Acetate, propionate, and butyrate are the prevalent SCFA produced in the human colon (Wang et al., 2004).

Figure 9:
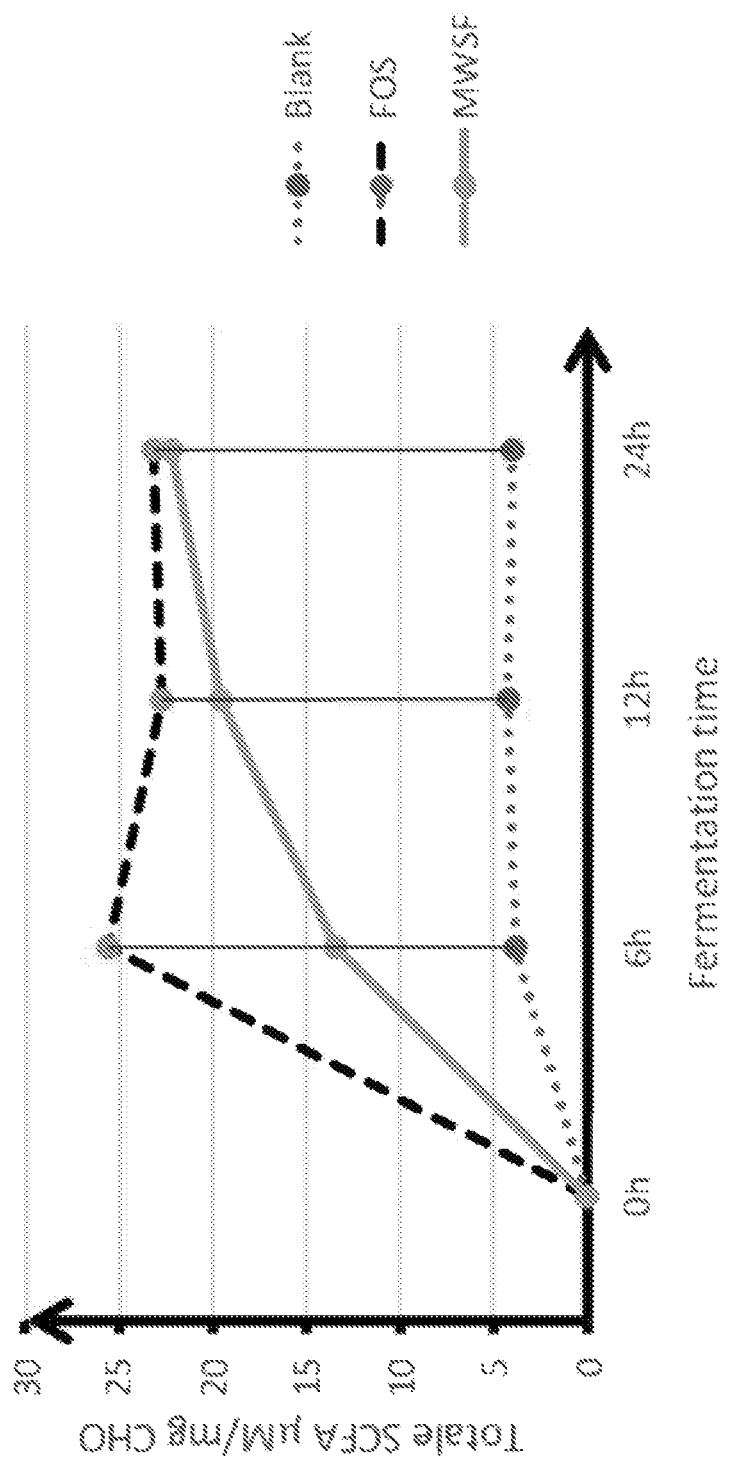
FIG. 9 is a schematic description of the total SCFA production during fermentation of a blank as a negative control, the FOS reference as a positive control, and the sample MWSF.

SCFA analysis data revealed that the microalgal water-soluble fiber fermented slowly and completely, whereas FOS fermented more rapidly. As illustrated in FIG. 9, the total SCFA produced by fermenting FOS was twice as high during the first 6 hours than by fermenting microalgal water-soluble fiber. At 12 hours of fermentation, the total SCFA was slightly higher with fermenting FOS than microalgal water-soluble fiber, but then they started to be similar after 24 hours of fermentation. An increase of total SCFA was noticed while fermenting microalgal water-soluble fiber. After the first 6 hours of fermentation 25 µM/mg fiber and 14 µM/mg were generated by FOS and microalgal water-soluble fiber (MWSF) samples respectively.

As illustrated in FIG. 9, fermentation of microalgal water-soluble dietary fiber resulted in a gradual increase in SCFA content during the 24 hour study comparative to FOS. FOS fermentation generated most of the SCFAs in the first 6 hours. These results confirm previous reports of rapid fermentation in FOS. Fermentation of microalgal water-soluble dietary fiber showed the lowest SCFA generation in the first 6 hours followed by a continuous increase, demonstrating a slow fermenting behavior.

This trend indicates a rapidly fermented FOS in the proximal colon and slow fermenting process of MWSF that takes enough time during the dietary fiber transit in the colon. MWSF can be fermented in the proximal and distal area of the colon. Moreover, this behavior is associated with a gradual production of SCFA. Total SCFA generation during MWSF fermentation is 14 µM/mg at 6 hours, 19 µM/mg at 12 hours, and then 24 µM/mg at 24 hours. SCFA can be then gradually absorbed by colon (gut) epithelium.

It is more likely that propionate and butyrate are playing a major role in the maintaining and improving colonic health. It had been reported that propionate improves colonic motility (Kvietis and Granger, 1981). The major SCFA in colon health, especially bowel health, is butyrate. Butyrate may influence transit time of dietary fibers and other non-digested food in the colon. Butyrate is a preferred energy source by colonocytes, than acetate and propionate (Cummings 1981). Butyrate improves bowel health by countering the proliferation of malignant cells.

Figure 10:
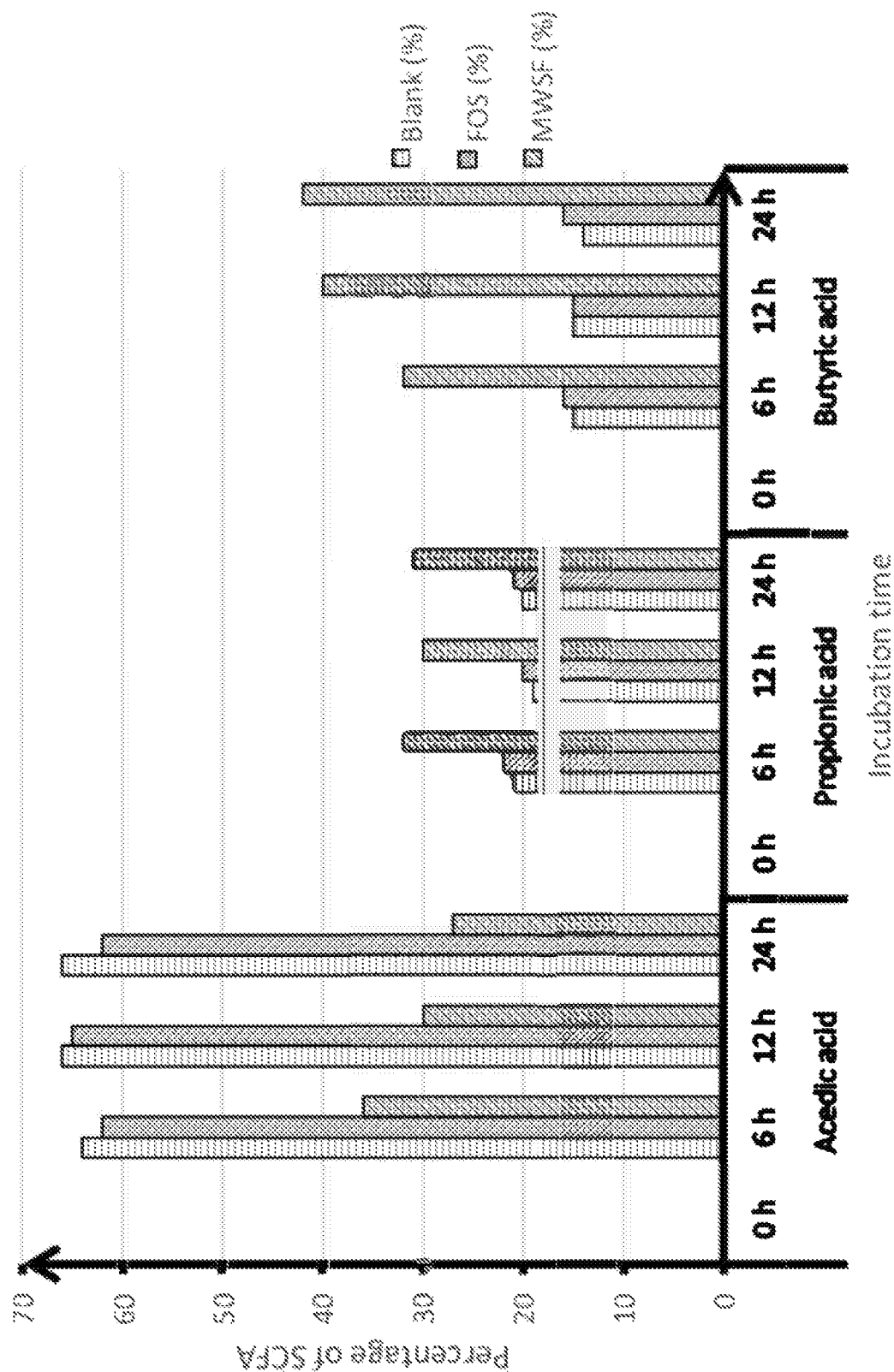
FIG. 10 is a schematic description of the SCFA profiles during fermentation of a blank as a negative control, the FOS reference as a positive control, and the sample MWSF.

As illustrated in FIG. 10, the fermentation of MWSF generates half the amount of acetate and twice the amounts of propionate and butyrate than FOS. Butyrate evidenced tumor-suppressive properties in colorectal cancer cells (Bultman et al., 2014). When dietary fibers are fermented, there is a generation of SCFAs, mainly acetate, propionate and butyrate. This ratio of these SCFAs generally depends on the gut microbiota composition and the nature of dietary fiber. There are dietary fibers that are producing less butyrate like what it was reported by Shin et al., 2015. Microalgal water-soluble dietary fibers (MWSF) are the type of fiber that promotes the growth of butyrate producing bacteria. For Acetate only 35 percent was generated by MWSF and 62 percent by FOS after the first 6 hours of fermentation. It was followed by 31 percent and 65 percent by MWSF and FOS respectively after 12 hours of fermentation. As shown, in FIG. 4 less propionate was generated by FOS along the fermentation period and it is around 21 percent comparatively to MWSF generates around 32 percent of propionate. Significant alteration of the SCFA ratio was observed with butyrate. Fermentation of MWSF produced a gradual increase in the SCFA ratio along the fermentation period (24 hours); from 32 percent at 6 hours to 42 percent at 24 hours by MWSF. FOS generated less butyrate as reported by previous studies, it was around 14 percent.

The idea of the present invention is to promote butyrate production in human gut microbiota by isolating butyrogenic dietary fiber. It had been reported that gut microbiota colonocytes relay on 60 to 70 percent of their energy on butyrate (Donohoe et al., 2011). Colonocytes are epithelial cells of the colon. Beta-oxidation of butyrate is performed in colonocyte mitochondria to generate energy and promote epithelial colon cell proliferation. Colonocytes continuously renew the intestinal epithelium. In contrast, colonic tumor cells do not use butyrate beta-oxidation. Instead, they use aerobic glycolysis. Butyrate improves symptoms of colonic inflammation. Its deficiency is associated with the development of inflammatory bowel disease (Hamer et al., 2008) due to the downregulation of pro-inflammatory pro-cytokines (Chang et al., 2014).

In the case of rapidly fermented dietary fiber, their carbon content is rapidly exhausted in the colon particularly in the proximal region. When they are exhausted, colon microbiota start to ferment other molecules such as proteins as a source of energy. Bacterial fermentation of proteins is different than dietary fibers. There is a concomitant change in the composition of gut microbiota. Proteins fermentation is called putrefaction, and it results in the production of a wide range of toxic metabolites including hydrogen sulfide, phenolic, and ammonia (Yao et al., 2016). Many of these metabolites are undesirable. For example, butyrate oxidation is inhibited by hydrogen sulfide. $H_2S$ blocks butyrate utilization by the colonic epithelial cells, which can result in the pathogenesis of ulcerative colitis (Windey et al., 2012). It had also been reported that histological damage to distal colonic mucosa is induced by ammonia (Mosele et al., 2015). Fiber availability in the distal region is more beneficial to the colon because it increases production of more SCFA (Pompei et al., 2008). The present invention teaches a slowly fermenting microalgal water-soluble dietary fiber that can be fermented by gut. The method utilizing the composition ensure that microbiota from both proximal and the distal colon have a substrate (microalgal dietary fiber) to metabolize. The method results in dominant dietary fiber fermentation in the distal area with less protein putrefaction. The method promotes the production of butyrate and improves colonic health by preventing damage and maintaining colonic epithelium.

Although the recommended daily intake range is about 25 g/day and about 38 g/day (Stephen et al., 2017), because the microalgal water-soluble dietary fibers are slowly fermentable they can be taken daily at a higher level. The method utilizes about 0.1 g/day to about 50 g/day, preferably about 5 to about 40 g/day. The daily intake is particularly about 25 to about 40 g/day. The microalgal water-soluble dietary fiber may be taken alone, as supplement or ingredient in food or beverages, and in liquid, paste, or solid form. The viscosity is about 50 centipoises to about 100000 centipoises, preferably about 1000 centipoises to about 50000 centipoises. Particularly, the viscosity is about 2500 centipoises to about 25000 centipoises.

The microalgal water-soluble dietary fiber can be mixed with other polysaccharides and other natural or synthetic chemicals in food, supplement, beverage, cosmetic, pharmaceutical products. The percentage of microalgal water-soluble polysaccharides in the mix with other components is about 0.1 percent to about 75 percent.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method to extract and isolate compounds from an algal biomass consisting of the steps:

physically treating, optionally preceded by a growth pretreatment of the algal biomass, the algal biomass by micro fluidization or ultra-sonication with a frequency greater than 20 KHz using a probe-type sonication or bath sonication, optionally in combination with extrusion using an extruder or with addition of a solvent, wherein the solvent is hexane, followed by centrifugation, wherein centrifugation of the physically treated biomass was performed at a speed of about 500 rpm to about 15000 rpm, followed by separating lipids and other oils at the top layer, the water soluble chemicals at the middle layer and the pellet at the bottom layer, hydrothermally treating the pellet by heating at alkaline pH, optionally in combination with pressure greater than 0.5 bar, while stirring, followed by centrifugation of the hydrothermally treated pellet at 2500 rpm for 10 minutes or 4000 rpm for 15 min, separating the supernatant from the resulting residue of the hydrothermally treated pellet, precipitating water-soluble polysaccharides from the supernatant, wherein the precipitated polysaccharides were washed and pH adjusted to about 7, and dried, and extracting carotenoids from the resulting residue using solvent, optionally including ultra-sonication or drying.

2. The method of claim 1, wherein the growth pretreatment is a starvation pre-treatment.

3. The method of claim 2, wherein the pre-treatment step further comprises use of physical and/or chemical treatments, or use of 0.5 g/L sodium nitrate and osmotic stress of NaCl 10 mM, during growth at pH 9 in darkness for 3 days.

4. The method of claim 1, wherein the carotenoid extraction step includes ultra-sonication.

5. The method of claim 1, wherein the water-soluble polysaccharides precipitating step uses either calcium salt solution or alcohol solution.

6. The method of claim 1 wherein the solvent in the carotenoid extracting step is hexane.

7. The method of claim 1, wherein the alkaline pH is obtained from NaOH/KOH molar ratio of about 0:4 to about 4:0.

8. The method of claim 1, wherein the alkaline pH is obtained from a base selected from the group consisting of sodium hydroxide, potassium hydroxide, calcium hydroxide, alkali metals, alkaline earth metals, ammonium hydroxide, ammonia, sodium carbonate, potassium carbonate, boron hydroxide, aluminum hydroxide, borax, amino alcohols and mixtures thereof.

9. The method of claim 1, wherein heating at alkaline pH is performed at a temperature about 60° C. to about 121° C. within the range of about 10 min to about 24 hours, or a pressure greater than 0.5 bar using an autoclave or pressure cooker, for about 5 min to about 60 min, and wherein the alkaline pH is obtained from a water solution including each of NaOH and KOH at the concentration about 0.5 M to about 4M.

10. The method of claim 1, wherein centrifugation of the physically treated biomass was performed at a speed of about 1000 rpm to about 10000 rpm.

11. The method of claim 1, wherein centrifugation of the physically treated biomass was performed at a speed of about 2000 rpm to about 5000 rpm.

12. The method of claim 5, wherein the water-soluble polysaccharides precipitating step uses either 10% calcium solution or 70% ethanol solution.

13. The method of claim 6, wherein the extracted carotenoids are dried.

14. The method of claim 7, wherein the NaOH/KOH molar ratio is about 1:3 to about 3:1.

15. The method of claim 7, wherein the NaOH/KOH molar ratio is about 2:2.

16. The method of claim 7, wherein the w/v ratio of pellet/alkaline solution is about 1:1 to about 100:1.

17. The method of claim 7, wherein the w/v ratio of pellet/alkaline solution is about 5:1 to about 50:1.

18. The method of claim 7, wherein the w/v ratio of pellet/alkaline solution is about 10:1 to about 20:1.

19. The method of claim 8, wherein amino alcohols are selected from the group consisting of ethanolamine, diethanolamine, triethanolamine, isopropanolamine, diisopropylamine, triisopropylamine, propylamine, 2-propylamine, methylamine, dimethylamine, trimethylamine, dimethylethanolamine, monoethylethanolamine, 2-(2-aminoethoxy) ethanol, diglycolamines, diethylamine and mixtures thereof.

20. The method of claim 9, wherein heating at alkaline pH is performed at a temperature about 80° C. to about 100° C.

21. The method of claim 9, wherein heating at alkaline pH is performed at either about 70° C. or 121° C.

22. The method of claim 9, wherein heating at alkaline pH is performed at a temperature of about 60° C. to about 121° C. within the range of about 60 min to about 12 hours.

23. The method of claim 9, wherein the heating at alkaline pH is performed at pressure greater than 0.5 bar for about 20 min to about 30 min.

24. The method of claim 9, wherein the water solution includes each of NaOH and KOH at the concentration about 1 M to about 2M.

* * * * *